US010150984B2

(12) United States Patent
Parker et al.

(10) Patent No.: US 10,150,984 B2
(45) Date of Patent: Dec. 11, 2018

(54) TYROSINE KINASE BIOSENSORS AND METHODS OF USE

(71) Applicant: Purdue Research Foundation, West Lafayette, IN (US)

(72) Inventors: Laurie L Parker, Minneapolis, MN (US); Andrew Michael Lipchik, Palo Alto, CA (US); Scott Charles Bolton, West Lafayette, IN (US)

( * ) Notice: Subject to any disclaimer, the term of this patent is extended or adjusted under 35 U.S.C. 154(b) by 0 days.

(21) Appl. No.: 15/358,320

(22) Filed: Nov. 22, 2016

(65) Prior Publication Data

US 2017/0342461 A1 Nov. 30, 2017

Related U.S. Application Data

(62) Division of application No. 13/761,968, filed on Feb. 7, 2013, now Pat. No. 9,499,854.

(60) Provisional application No. 61/736,312, filed on Dec. 12, 2012, provisional application No. 61/704,298, filed on Sep. 21, 2012, provisional application No. 61/693,002, filed on Aug. 24, 2012, provisional application No. 61/605,591, filed on Mar. 1, 2012, provisional application No. 61/603,752, filed on Feb. 27, 2012, provisional application No. 61/595,959, filed on Feb. 7, 2012.

(51) Int. Cl.
*C12Q 1/48* (2006.01)

(52) U.S. Cl.
CPC .................................. *C12Q 1/485* (2013.01)

(58) Field of Classification Search
None
See application file for complete search history.

(56) References Cited

U.S. PATENT DOCUMENTS

2011/0046018 A1 2/2011 Chen et al.

OTHER PUBLICATIONS

Schaefer et al (1998 Analytical Biochemistry 261:100-112).*
Akiba, et al., Selective Detection of Phosphotyrosine in the Presence of Various Phosphate-Containing Biomolecules with the Aid of a Terbium (III) Complex, ChemBioChem, 2009,vol. 10, p. 1773-1776.
Akiba, et al., Binuclear Terbium (III) Complex as a Probe for Tyrosine Phosphorylation, Chem. Eur. J., 2010, vol. 16, p. 5018-5025.
Amanchy, et al., Identification of Novel Phosphorylation Motifs Through an Integrative Computational and Experimental Analysis of the Human Phosphoproteome, J Proteomics Bioinform, vol. 4, Iss. 2, p. 022-035.
Atkinson, et al., A Cationic Lanthanide Complex Binds Selectively to Phosphorylated Tyrosine Sites, Aiding NMR Analysis of the Phosphorylated Insulin Receptor Peptide Fragment, Org. Biomol. Chem., 2006, vol. 4, p. 3166-317.
Balakrishnan, et al., Design of a Protein Kinase-Inducible Domain, J. Am. Chem. Soc., 2006, vol. 128, p. 5590-5591.
Chen, et al., Discovery of Protein Phosphorylation Motifs through Exploratory Data Analysis, PLos One, vol. 6, Iss. 5, p. 1-15.
Dang, et al., Prediction of Kinase-Specific Phosphorylation Sites Using Conditional Random Fields, Bioinformatics, 2008, vol. 24, Iss. 24, p. 2857-2864.
He, et al., Motif-All: Discovering All Phosphorylation Motifs, BMC Bioinformatics, 2011, vol. 12, Iss. 1, p. 1-8.
Horton, et al., Multiplexing Terbium- and Europium-Based TR-FRET Readouts to Increase Kinase Assay Capacity, Journal of Biomolecular Screening, 2010, vol. 15, Iss. 8, p. 1008-1015.
Jung, et al., PostMod: Sequence Based Prediction of Kinase-Specific Phosphorylation Sites with Indirect Relationship, BMC Bioinformatics, 2010, vol. 11, Iss. 1, p. 1-10.
Li, et al., Prediction of Kinase-Specific Phosphorylation Sites with Sequence Features by a Long-Odds Ratio Approach, Proteins, 2008, vol. 70, p. 404-414.
Linding, et al., NetworKIN: A Resource for Exploring Cellular Phosphorylation Networks, Nucleic Acids Research, 2008, vol. 36, p. D695-D699.
Liu, et al., Phosphorylation-Dependent Metal Binding by α-Synuclein Peptide Fragments, J. Bid. Chem., 2007, vol. 12, p. 234-247.
Liu, et al., Phosphorylation of an α-Synuclein Peptide Fragment Enhances Metal Binding, J. Am. Chem. Soc., 2005, vol. 127, p. 9662-9663.
Miller, et al., Linear Motif Atlas for Phosphorylation-Dependent Signaling, Science Signaling, 2008, vol. 1, Iss. 35, p. 1-11.
Neuberger, et at., pkaPS: Prediction of Protein Kinase A Phosphorylation Sites with the Simplified Kinase-Substrate Binding Model, Biology Direct, 2007, vol. 2, lss. 1, p. 1-23.
Nitz, et al., A Powerful Combinatorial Screen to Identify High-Affinity Terbium (III)—Binding Peptides, Chem. Bio. Chem., 2003, vol. 4, p. 272-276.
Obenauer, et al., Scansite 2.0: Proteome-Wide Prediction of Cell Signaling Interactions Using Short Sequence Motifs, Nucleic Acids Research, 2003, vol. 31, Iss. 13, p. 3635-3641.
Pazos, et al., Detection of Phosphorylation States by Intermolecular Sensitization of Lanthanide-Peptide Conjugates, Chem. Commun., 2012, vol. 48, p. 9534-9536.
Saunders, et al., Predikin and PredikinDB: A Computational Framework for the Prediction of Protein Kinase Peptide Specificity and an Associated Database of Phosphorylation Sites, BMC Bioinformatics, 2008, vol. 9, p. 1-11.
Saunders, et al., The Predikin Webserver: Improved Prediction of Protein Kinase Peptide Specific Using Structural Information, Nucleic Acids Research, 2008, vol. 36, p. W286-W290.
Sculimbrene, et al., Lanthanide-Binding Tags as Luminescent Probes for Studying Protein Interactions, J. Am. Chem. Soc., 2006, vol. 128, p. 7346-7352.
Sobolev, et al., Functional Classification of Proteins Based on Projection of Amino Acid Sequences: Application for Prediction of Protein Kinase Substrates, BMC Bioinformatics, 2010, vol. 11, p. 1-18.

(Continued)

*Primary Examiner* — Christopher M Gross
(74) *Attorney, Agent, or Firm* — D'Hue Law; Cedric A. D'Hue

(57) ABSTRACT

Disclosed are compositions and methods for measuring tyrosine kinase activity.

8 Claims, 8 Drawing Sheets

Specification includes a Sequence Listing.

(56) References Cited

OTHER PUBLICATIONS

Tremblay, et al., A Luminescent Sensor for Tyrosine Phosphorylation, Organic Letters, 2008, vol. 10, No. 1, p. 5-8.

Tremblay, et al., Phosphorylation State-Responsive Lanthanide Peptide Conjugates: A Luminescence Switch Based on Reversible Complex Reorganization, Organic Letters, 2006, vol. 8, Iss. 13, p. 2723-2726.

Xue, et al., GPS: A Comprehensive www Server for Phosphorylation Sites Prediction, Nucleic Acids Research, 2005, vol. 33, p. W184-W187.

Xue, et al., GPS 2.0, a Tool to Predict Kinase-Specific Phosphorylation Sites in Hierarchy, Molecular & Cellular Proteomics 7.9, 2008, p. 1598-1608.

Wong, et al., KinasePhos 2.0: A Web Server for Identifying Protein Kinase-Specific Phosphorylation Sites Based on Sequences and Coupling Patterns, Nucleic Acids Research, 2007, vol. 35, p. W588-W594.

Zondlo, et al., Design of art Encodable Tyrosine Kinase-Inducible Domain: Detection of Tyrosine Kinase Activity by Terbium Luminescence, J. Am. Chem. Soc., 2010, vol. 132, p. 5619-5621.

USPTO, Notice of Allowance dated Oct. 12, 2016 for U.S. Appl. No. 13/761,968, Alexandria, Virginia.

USPTO, Notice of Allowance dated Sep. 9, 2016 for U.S. Appl. No. 13/761,968, Alexandria, Virginia.

USPTO, Amendment after Non-Final Office Action dated Aug. 15, 2016 for U.S. Appl. No. 13/761,968, Alexandria, Virginia.

USPTO, Non-Final Office Action dated Aug. 12, 2016 for U.S. Appl. No. 13/761,968, Alexandria, Virginia.

USPTO, Amendment after Final Office Action dated Jul. 8, 2016 for U.S. Appl. No. 13/761,968, Alexandria, Virginia.

USPTO, Advisory Action dated Jul. 7, 2016 for U.S. Appl. No. 13/761,968, Alexandria, Virginia.

USPTO, Amendment after Final Office Action dated Jul. 7, 2016 for U.S. Appl. No. 13/761,968, Alexandria, Virginia.

USPTO, Amendment after Final Office Action dated Jun. 9, 2016 for U.S. Appl. No. 13/761,968, Alexandria, Virginia.

USPTO, Final Office Action dated Mar. 10, 2016 for U.S. Appl. No. 13/761,968, Alexandria, Virginia.

USPTO, Amendment after Non-Final Office Action dated Oct. 29, 2015 for U.S. Appl. No. 13/761,968, Alexandria, Virginia.

USPTO, Non-Final Office Action dated Jul. 2, 2015 for U.S. Appl. No. 13/761,968, Alexandria, Virginia.

USPTO, Response to Restriction Requirement dated Apr. 29, 2014 for U.S. Appl. No. 13/761,968, Alexandria, Virginia.

USPTO, Restriction Requirement dated Feb. 5, 2014 for U.S. Appl. No. 13/761,968, Alexandria, Virginia.

USPTO, Preliminary Amendment dated Nov. 1, 2013 for U.S. Appl. No. 13/761,968, Alexandria, Virginia.

Bechara, et al, Cell-penetrating peptides: 20 years later, where do we stand?, 2013, pp. 1693-1702, FEBS Letters 587, Federation of European Biochemical Societies (FEBS), Heidelberg, Germany.

\* cited by examiner

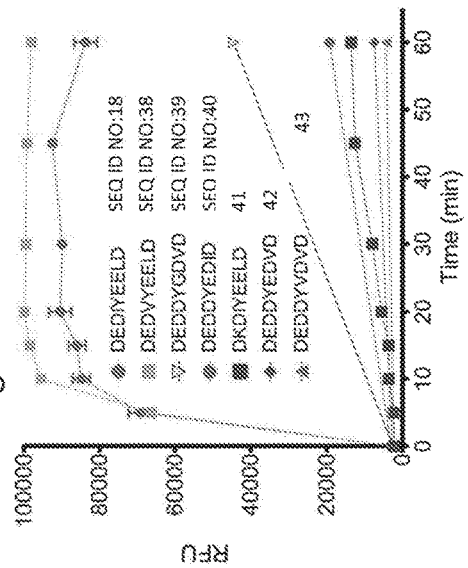
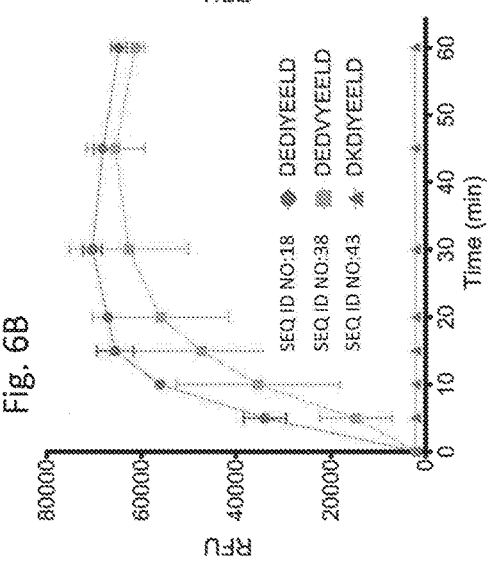
Fig. 6A, Fig. 6B, Fig. 6C

TYROSINE KINASE BIOSENSORS AND METHODS OF USE

CROSS-REFERENCE TO RELATED APPLICATIONS

This application is a divisional application of U.S. patent application serial number 13/761,968, filed Feb. 7, 2013 which claims the benefit of priority to U.S. provisional application numbers 61/595,959 filed Feb. 7, 2012, 61/603,752 filed Feb. 27, 2012, 61/605,591 filed Mar. 1, 2012, 61/693,002 filed. Aug. 24, 2012, 61/704,298 filed. Sep. 21, 2012, and 61/736,312 filed Dec. 12, 2012, each of which is incorporated by reference in its entirety.

STATEMENT REGARDING FEDERALLY SPONSORED RESEARCH OR DEVELOPMENT

This invention was made with governments support under Grant Nos. R25CA128770, R00CA127161, CA037372, and R21CA160129 awarded by the National Institutes of Health, National Cancer Institute. The United States Government has certain rights in the invention.

SEQUENCE LISTING

Incorporated by reference in its entirety herein is a computer-readable sequence listing electronically filed with this application.

INTRODUCTION

Spleen tyrosine kinase (Syk) is a 72 kDa non-receptor tyrosine kinase first isolated from bovine thymus and porcine spleen best known for its role in B lymphocyte development and activation. Loss of Syk expression results in perinatal lethality in mice and an arrest in the development of B cells. Upon antigen binding to B cell antigen receptor (BCR), Lyn, a Src family kinase, initiates phosphorylation of immunoreceptor tyrosine-based activation motifs (ITAMs) on components of the BCR. Phosphorylation of the ITAMs results in recruitment and activation of Syk, and phosphorylation of multiple Syk tyrosine residues. Following activation of Syk, numerous signaling pathways are initiated, leading to activation of downstream transcription factors, ultimately resulting in induction of cell proliferation and differentiation.

Dysregulation of the expression or the activity of Syk contributes to various disease states, making it a potential therapeutic target. Syk has been implicated as a factor in rheumatological disorders (such as rheumatoid arthritis) and malignant diseases of myeloid, lymphocytic and epithelial origin. For example, Syk was found to be constitutively active in primary blasts from a set of patients with acute myeloid leukemia (AML). Inhibition of Syk decreased the viability of these AML blasts in vitro and reduced the number of these cells infiltrating spleen and bone marrow in a mouse xenograft model. In some chronic lymphocytic leukemia cells (B-CLL), Syk is hyperactive despite exhibiting normal expression levels, and inhibition of Syk or silencing of Syk expression via siRNA decreases cell viability. Further, several peripheral T-cell lymphomas (PTCLs) exhibit aberrant expression of Syk. In these cells, siRNA silencing of Syk translation or inhibition of its kinase activity with a specific kinase inhibitor (R406, Rigel Pharmaceuticals) induces apoptosis and blocks proliferation in cells with elevated Syk Y525/Y526 phosphorylation. These results suggest that Syk could be a novel therapeutic target for the treatment of PTCLs. Conversely, in breast cancer, which has an epithelial origin. Syk appears to have tumor suppressor functions, in that Syk is expressed in normal breast epithelia, whereas there is little to no Syk present in metastatic breast cancer cells. Expression of Syk negatively affects motility and invasion in these carcinomas.

The ability to measure Syk activity would guide treatment of certain cancers and facilitate development of novel therapeutics. Methods of measuring Syk activity currently in use include in vitro kinase assays, luciferase reporter assays of downstream transcription factors, and phosphotyrosine antibody-based detection. Each of these methods has drawbacks that make them less than optimal for the clinical setting. In vitro kinase assays measure Syk activity post lysis. Therefore, if using a whole cell lysate, proteins such as c-Cbl that normally modulate the function of the kinase (and which are known to be critical for obtaining biologically-relevant activation especially for Syk) can become separated from Syk; also, proteins normally found in different subcellular compartments could artifactually interact with Syk and alter its activity. Also, as a result of phosphatase activity and Syk autophosphorylation, the state of phosphorylation and activity of Syk can change during in vitro kinase assays in ways that may not be relevant to its intracellular activity in a disease context. While transcription factor-driven luciferase reporter assays are performed in whole cells, they are an indirect measure of Syk activity as there are numerous proteins in the pathways between Syk and the transcription factors and thus may be confounded by disruption of additional components of these cascades. Phosphotyrosine antibody-based methods such as Western blots and Phosphoflow cytometry use phosphorylation sites in endogenous proteins, such as known Syk-targeted sites and/or Syk autophosphorylation sites, as surrogate reporters of Syk activity. However, phosphorylation at endogenous sites may be occurring from kinases other than Syk, such as Lyn, so specificity can be difficult to confirm. Additionally, Syk is phosphorylated on multiple sites including some that negatively regulate the kinase. Besides this, antibodies for every potentially meaningful site of Syk phosphorylation are not available, and their development is subject to the uncertainties inherent in epitope and antibody generation. Therefore, an ideal method to measure Syk activity would be one that specifically monitors the ability of the kinase to catalyze a phosphotransferase reaction in an intact cell.

There is a need in the art for compositions and methods of measuring activity of tyrosine kinases, including Syk kinase. The compositions and methods described herein address that need.

SUMMARY

The present invention relates generally to compositions and methods for assaying tyrosine kinase activity, and to methods for identifying suitable peptide sequences for use in the assays.

In certain embodiments, the invention includes a biosensor comprising a peptide comprising a substrate sequence, i.e., an amino acid sequence including a tyrosine residue that can be phosphorylated by a tyrosine kinase. In certain embodiments, the biosensor includes a substrate sequence that can be phosphorylated by Syk, Btk, one or more Src family tyrosine kinases, Jak2, or Abl. In certain embodiments, the biosensor includes one or more additional functional elements. In some embodiments, the functional elements include an affinity tag to facilitate capture, isolation or immobilization of the biosensor, and/or a cleavable linker, and/or a cell penetrating peptide. In certain embodiments, the biosensor may include an affinity tag, such as biotin or a poly-His tag. In certain embodiments, the biosensor may include a cell penetrating peptide. In certain embodiments, the cell penetrating peptide may be Tat. In certain embodiments, the biosensor may include such as a cleavable linker, such as a photocleavable linker. The photocleavable linker may include, for example, a photocleavable amino acid analog such as beta(nitrophenyl)alanine. The photocleavable linker covalently links two other elements of the biosensor. For example, the substrate sequence may be linked to an affinity tagged peptide sequence which is in turn linked through a photocleavable linker to a cell penetrating peptide. In other embodiments, the biosensor is designed to include photocleavable linker between the substrate sequence and affinity tag.

In certain embodiments, the biosensor comprises a substrate sequence for Syk, Btk, one or more Src family tyrosine kinases, Jak2, or Abl.

In certain embodiments, the composition may include a Syk-specific biosensor comprising a substrate sequence selected from the group consisting of DEEDYEEPD (SEQ ID NO:1), DEEDYEEPDEP (SEQ ID NO:2), EEDDYESPN (SEQ ID NO:3), EEDSYESPN(SEQ ID NO:4), EEDSYDSPN(SEQ ID NO:5), EEDDYESPNEP (SEQ ID NO:6), EEDSYESPNEP (SEQ ID NO:7), EEDSYDSPNEP (SEQ ID NO:8), GGEEDDYESPNEPGG (SEQ ID NO:9), GGEEDSYESPNEPGG (SEQ ID NO:10), GGEEDSYDSPNEPGG (SEQ ID NO:11), GGDEEDYEEPDEPGG (SEQ ID NO:12), and is GGEEDSYDSPNGG (SEQ ID NO:13).

In certain embodiments, the composition may include a Btk-specific biosensor that includes ELDAYLENE (SEQ ID NO:14), ELAGYLENE (SEQ ID NO:15), ELDVYEEQL (SEQ ID NO:16), or ELDVYVEQT (SEQ ID NO:17).

In certain embodiments, the composition may include a Src family-specific biosensor that has includes DEDIYEELD (SEQ ID NO:18), EGDVYDFVE (SEQ ID NO:19), NNDVYEQPE (SEQ ID NO:20), EEDVYDMPD (SEQ ID NO:21), EADVYDMPD (SEQ ID NO:22), DLDIYEELD (SEQ ID NO:23), or EAHVYDMMD (SEQ ID NO:24).

In certain embodiments, the composition may include a Jak2-specific biosensor that has includes DPDRYIRTE (SEQ ID NO:25), EGDRYLKLE (SEQ ID NO:26), EDGRYVQLD (SEQ ID NO:27), or PKPRYVQLD (SEQ ID NO:28).

In certain embodiments, the composition may include an Abl-specific biosensor that includes DEVAYQAPF (SEQ ID NO:29), DFIRYHFWV (SEQ ID NO:30), DHIFYIIPV (SEQ ID NO:31), or DHIFYHIPV (SEQ ID NO:32).

In other embodiments are provided methods for detecting tyrosine kinase activity. In certain embodiments, the methods allow detection of the activity of Syk, Btk, one or more Src family tyrosine kinases, Jak2, or Abl by detecting phosphorylation of a substrate sequence of Syk, Btk, a Src family kinase, Jak2, or Abl. In certain embodiments, the methods allow "multiplexing" of the detection of tyrosine kinase activity, i.e., detecting the activity of two or more tyrosine kinases in a single reaction. In certain embodiments, the assay is conducted in vitro or in whole cells. In certain embodiments, phosphorylation is detected using ELISA, terbium based time-resolved luminescence, MALDI-TOF MS analysis, or multiple reaction monitoring (MRM) on a triple quadrupole mass spectrometer. In certain embodiments, the method is conducted using a substrate sequence or a biosensor comprising the substrate that covalently attached directly or indirectly through an affinity tag to a solid surface, such as a bead, a multi-well plate, or nanoparticle.

In certain embodiments, the methods of the invention may be used to determine the level of tyrosine kinase activity in a biological sample from a mammal, such as a human. In certain embodiments, the methods involve detecting Syk activity in a sample from a person suspected of having or risk for developing a condition associated with altered tyrosine kinase activity increased, i.e., tyrosine kinase activity that is increased or decreased relative to the tyrosine kinase activity of a control, e.g., a sample from a person who does not have the condition, or a normal range of tyrosine kinase activity based on the tyrosine kinase activities of samples from a relevant sample of people. In certain embodiments, the sample includes lymphocytic cells, myeloid cells, or cancer cells of epithelial origin. In certain embodiments, the results of the determination may be used in diagnosis or prognosis, or in determining a course of treatment.

In certain embodiments, the methods involve determining the level of Syk activity in a person. In certain embodiments, the person has acute myeloid leukemia (AML). In certain embodiments, the method may involve recommending treatment or treating a person with AML having an increased level of Syk activity relative to a control with a Syk inhibitor. In certain embodiments, the method involves determining the level of Syk activity in a person with chronic lymphocytic leukemia cells (B-CLL). In certain embodiments, the method may involve recommending treatment or treating a person with B-CLL having an increased level of Syk activity relative to a control with a Syk inhibitor Syk. In certain embodiments in which the person has a disorder associated with increased Syk activity, treatment may include administering to the person an effective amount of a Syk inhibitor, such as an siRNA or small molecule Syk inhibitor, some of which are known in the art. In certain embodiments, the method may involve recommending treatment or treating a person with peripheral T-cell lymphomas (PTCLs) In certain embodiments in which the person has a disorder associated with increased Syk activity, treatment may include administering to the person an effective amount of a Syk inhibitor, such as an siRNA or small molecule Syk inhibitor, some of which are known in the art.

In certain embodiments, the methods involve determining the level of Syk activity in a sample from a person with breast cancer. In certain embodiments, the method involves recommending treatment or treating a person with breast cancer cells having reduced expression of Syk, the treatment including administering an effective amount of a Syk agonist, a Syk kinase, or a genetic construct expressing Syk kinase.

In certain embodiments, the methods can be used to determine whether a person with a cancer is likely to benefit from a particular treatment. For example, in certain embodiments, the methods of the invention can be used to detect tyrosine kinase activity in whole cells obtained from the person in the presence and absence of an inhibitor of the tyrosine kinase. In certain embodiments, the methods employ an Abl biosensor to measure phosphorylation of in whole cells from a person with chronic myelogenous leukemia (CML) to assess whether the cells are sensitive or resistant to treatment with imatinib. In certain embodiments, phosphorylation levels of cells treated or not treated with imatinib in vitro are compared, with the absence of a sufficient decrease in phosphorylation of the substrate sequence from imatinib treated cells suggesting that the cancer may not respond to treatment with the inhibitor. In other embodiments, samples are taken from the person with CML at different times to monitor effectiveness as measured by a sustained decrease in phosphorylation of the Abl biosensor following treatment with imatinib. In certain embodiments, the methods are performed using MRM on a triple quadrupole mass spectrometer using relatively few cells, e.g., from 10,000 to 50,000 cells, making testing of clinical samples feasible.

In other embodiments, the methods of the invention can be used to screen for molecules capable of altering tyrosine kinase activity, including molecules that reduce or increase tyrosine kinase activity. In certain embodiments are provided methods for screening for inhibitors of Syk, Btk, one or more Src family tyrosine kinases, Jak2, or Abl. In certain embodiments, the assays are conducted in a high throughput format. In certain embodiments, the methods employ whole cells that are contacted with the biosensor in the presence and absence of the test molecule to assess whether the agent inhibits intracellular phosphorylation of the substrate sequence.

In certain embodiments are provided kits comprising peptide substrates, for example, peptide substrate immobilized on a solid surface, or comprised within a biosensor. In certain embodiments, the kits may be used to perform the methods of the invention. In certain embodiments, the kits may contain additional components, including, for example, suitable buffers, Syk, and a phosphorylation detection reagent such as antibodies or terbium.

In certain embodiments, the present invention includes a method for designing peptide substrates for a kinase. The method may be used to identify substrates for tyrosine kinases and serine/threonine kinases. The method involves calculating a positional scoring matrix (PSM) using a positional probability matrix of using sequence of known substrates and empirical data developed using a positional screening peptide library. In some embodiments, the PSM is used to generate a kinase-focused peptide library. The members of the library are assayed for the ability to serve as a substrate for the tyrosine kinase of interest, and are screened using other kinases to identify substrates specific for the kinase of interest.

In certain embodiments, sequences with high PSM are aligned with a terbium binding motif, and selected for inclusion in the kinase-focused peptide library based on similarity to the motif or are modified to enhance activity.

In certain embodiments, the kinase focused library is screened for the ability to bind terbium in a phosphorylation dependent manner.

BRIEF DESCRIPTION OF THE DRAWINGS

FIG. 6A shows sequences of potential kinase substrates and scores for Lyn and Src.

FIG. 6B is an ELISA readout for time course assays for Lyn kinase using three peptides.

FIG. 6C is an ELISA readout for timecourse assays Src kinase assays using seven peptides.

DETAILED DESCRIPTION

Figure 1:
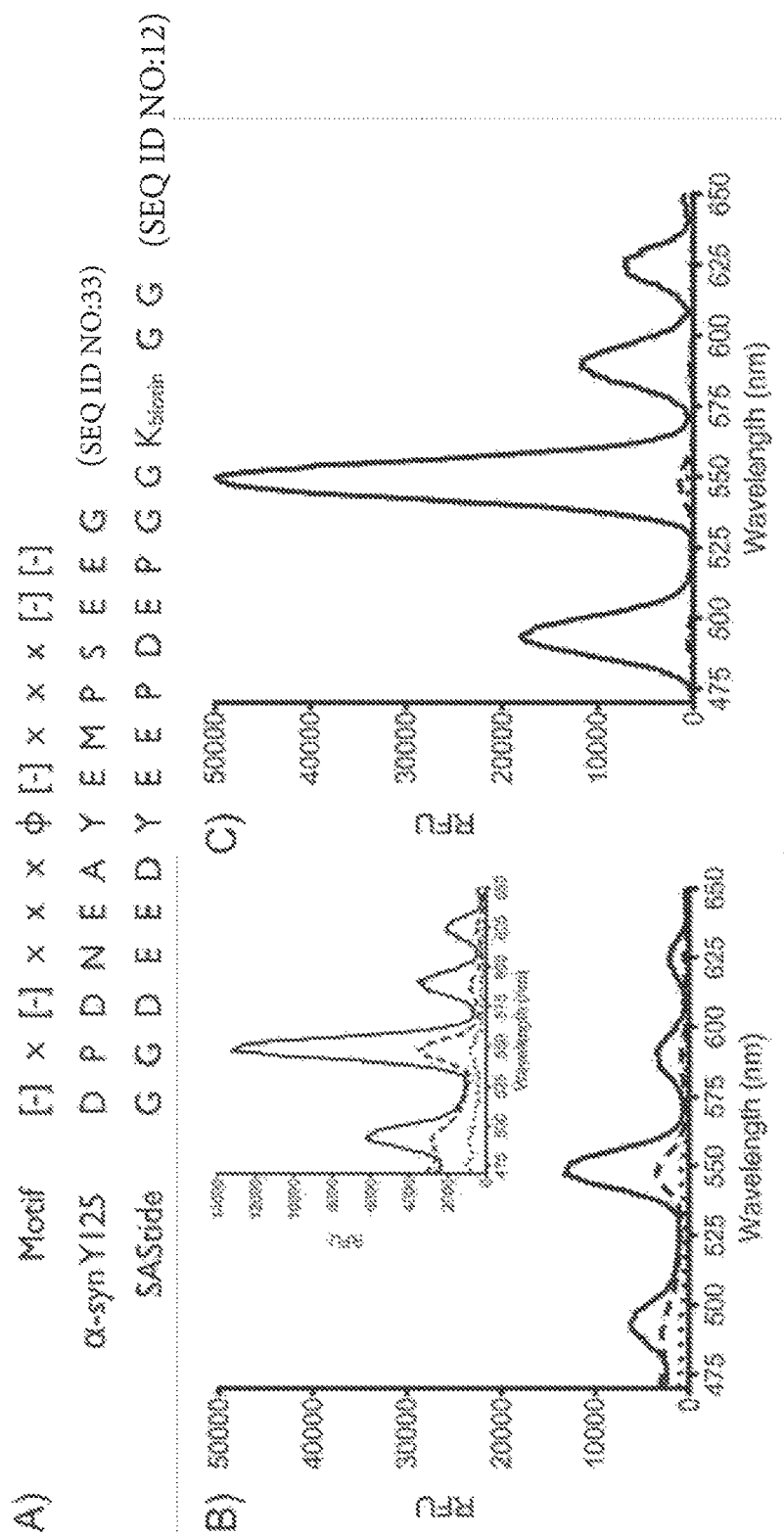
FIG. 1A shows the sequence alignment of a peptide from α-synuclein (α-syn Y125) an atypical sensitizing peptide, and SAStide.
FIG. 1B shows steady-state luminescence plots for SAStide and pSAStide and Tb.
FIG. 1C shows time-resolved luminescence emission pSAStide, SAStide, and Tb.

The methods and compositions provide for direct and specific monitoring of intracellular tyrosine kinase activity in physiological contexts. A Syk-specific biosensor peptide was developed by combining a Syk-specific peptide based on a Syk substrate sequence, identified using a bioinformatics approach, with other modular units including a biotinylated lysine for affinity capture of the substrate and a cell penetrating peptide for delivery of the biosensor into cells. This Syk kinase peptide biosensor (SAStide) did not cause toxicity at the concentration used in these studies, and was able to detect dose-dependent and time-dependent activation and inhibition of endogenous Syk using physiologically relevant stimuli in cultured cell lines as well as primary splenic mouse B cells. These results demonstrate the potential for this strategy to be used in a multiwell plate ELISA assay to analyze Syk activity in contexts that could include study of signaling processes in a basic research setting and monitoring therapeutic response in translational applications.

The SAStide biosensor was demonstrated to work in a complex, biologically-relevant system using Syk-deficient DT40 chicken B cells. Syk plays a key role in B cell signaling, but is partly dependent upon activation of Lyn through antigen binding to the BCR. Stimulation of Syk-deficient cells by cross-linking the heavy chain of the BCR in the presence and absence of $H_2O_2$ allowed for the specificity of the biosensor to be assessed in the context of Lyn kinase activation. In the absence of Syk, phosphorylation of the biosensor was not increased above background levels and did not change over time following BCR engagement in the absence of Syk, even when overall tyrosine kinase signaling was amplified as a result of $H_2O_2$ exposure. Syk also plays a major role in oxidative stress signaling, and its activation during oxidative stress is the result of both its own activity (via autophosphorylation) as well as other protein tyrosine kinases. Other kinases also become activated during oxidative stress (as observed via antiphosphotyrosine blotting), yet there was no increase in phosphorylation of the biosensor in the absence of Syk under these conditions. Reconstitution of the Syk deficient cells with Syk-EGFP resulted in phosphorylation of the biosensor peptide under B cell receptor-activating conditions and in the presence of oxidative stress. This suggests that even in a complex cellular environment, the Syk biosensor is selectively phosphorylated by Syk and not by Lyn or other activated tyrosine kinases in these cells. Together these results demonstrate that the biosensor is specific for the detection of Syk activity in B cells and B cell model systems.

The compositions and methods of the invention offer the ability to monitor kinase activation and inhibition by compounds such as piceatannol and dasatinib in an intact cell. Isolation of a kinase from the cellular environment can alter its function by removing regulatory proteins, eliminating alternatively spliced variants, altering post-translational modifications and/or disrupting subcellular compartmentalization. Additionally, isolation of the kinase precludes evaluation of the contribution of off-target effects of the drug, which could potentially affect efficacy (positively or negatively) via inhibition of upstream signaling in addition to the direct inhibition of the target.

Using the SAStide biosensor, inhibition of endogenous intracellular Syk activity in a dose-dependent manner by the Src-family kinase inhibitors, dasatinib, and piceatannol was detected.

Aside from its potential utility in basic research on the function of Syk kinase, the straightforward workflow and compatibility of this biosensor substrate with the multiwell ELISA-style readout might be useful in a translational setting to determine Syk kinase pharmacodynamics in patient B cell populations.

In accordance with one embodiment, kinase specific substrate peptides, e.g., Syk-, Btk-, a Src family kinase-, Jak2-, or Abl-specific substrate peptides, were designed, synthesized, and screened for the ability to be phosphorylated by their respective specific kinases. These substrates can be used to identify and quantitate specific kinase activity either in vitro or in vivo. In accordance with one embodiment, the substrate peptide is introduced into cells and subsequently recovered to indicate the kinase activity in a living cell. In accordance with one embodiment, the substrate peptide is introduced into the cell using any method, including any of several standard techniques known in the art, including, for example, microinjecting, electroporating, optoporating, vesicle fusing, pinocytic loading, or associating said substrate molecules with membrane permeant peptides. In accordance with one embodiment the substrate peptide is linked to a cell penetrating peptide. In one embodiment the substrate peptide is covalently linked to a cell penetrating peptide, optionally through a cleavable linker, to form a biosensor that will be taken up by living cells.

In some embodiments, the kinase substrate peptide can be linked to a cell penetrating peptide to form a biosensor that can be used to measure specific kinase activity in living cells. In one embodiment the cell penetrating peptide (CPP) is a protein transduction domain or a fragment thereof. Examples of useful CPPs include, but are not limited to, the TAT peptide (SEQ ID NO:35), and the protein transduction domains of Penetratin (pAntp) (SEQ ID NO:48), Transportan (SEQ ID NO:50), MPG (SEQ ID NO:49), MPGdeltaNLS (SEQ ID NO:50), and pHLIP (SEQ ID NO:52). Cell penetrating fragments of CPPs can also be used in a delivery system and/or method of the invention. As used herein, the term CPP includes cell penetrating fragments of protein transduction domains. In accordance with tone embodiment the cell penetrating peptide comprises the sequence of RKKRRQRRR (SEQ ID NO:35). In certain embodiments, the CPP can comprise or consist of D-amino acids and/or L-amino acids. For example, a CPP can consist entirely of D-amino acids or entirely of L-amino acids; or a CPP can comprise a mixture of D- and -amino acids.

In certain embodiments, the amino acid sequence of a CPP can be in the forward direction (i.e. a native peptide) or in the reverse direction. As used herein, reference to a CPP includes both the native and reverse sequences. In one embodiment, the reverse sequence can be a retro-inverso peptide (i.e. the amino acid sequence is the reverse of the native sequence, and consists of D-amino acids). For example, the term "TAT peptide" as used herein includes a retro-inverso TAT peptide comprising a reverse sequence of the protein transduction domain (PTD) of the HIV-1 TAT protein. Examples of other suitable CPPs include, without limitation, the PTD of Penetratin (pAntp), Transportan, MPG, MPGdeltaNLS, and pHLIP.

In certain embodiments, the biosensor includes the substrate sequence linked to one or more tags to facilitate purification of the biosensor and/or to adhere the biosensor to a substrate. In one embodiment the tag is a peptide tag such as His6 (six consecutive histidine residues). In an alternative embodiment the tag is an antigen or biotin. In certain embodiments, the biosensor includes a substrate sequence, a tag, and a CPP.

In certain embodiments, the methods can be used to predict responsiveness of a cancer to a therapeutic treatment using relatively few cells. For example, Bcr-Abl plays a major role in the pathogenesis of chronic myelogenous leukemia (CML), and is the target of the breakthrough drug imatinib. Although most patients respond well to imatinib, approximately 30% never achieve remission or develop resistance within 1-5 years of starting imatinib treatment. Evidence from clinical studies suggests that achieving at least 50% inhibition of a patient's Bcr-Abl kinase activity (relative to their level at diagnosis) is associated with improved patient outcomes, including reduced occurrence of resistance and longer maintenance of remission. In certain embodiments, a Bcr-Abl kinase activity assay is described that can be used to predict or monitor response to imatinib using MRM on a triple quadrupole mass spectrometer. MRM enabled reproducible, selective detection of the peptide biosensor at fmol levels from aliquots of cell lysate equivalent to ~15,000 cells. This degree of sensitivity facilitates the miniaturization of the entire assay procedure down to cell numbers approaching 15,000, making it practical for translational applications in patient cells in which the limited amount of available patient material often presents a major challenge.

EXAMPLES

Materials and Methods

Cell culture and biological reagents. The DG75 and DT40 B cell lines were grown to a density of $0.4 \times 10^6$ cells/mL in RPMI-1640 medium containing 7.5% FBS, 1 mM sodium pyruvate, 100 IU/mL penicillin, 100 μg/mL streptomycin and 50 μM 2-metcaptoethanol. Additionally, DT40 cell medium contained 1% chicken serum. Anti-chicken IgM and anti-mouse IgM F(ab')$_2$ fragments were purchased from Bethyl Laboratories. Anti-human IgM was purchased from Rockland Immunochemicals. Hydrogen peroxide was purchased from Mallinckrodt. Anti-Syk (N-19) was purchased from Santa Cruz Biotechnology. Anti-tubulin and anti-phosphotyrosine (4G10) were purchased from Millipore. Anti-phospho Syk (Y525/526) was purchased from Cell SignalingTechnology.

Peptide Synthesis and Purification. Peptides were synthesized using 'Fast' Fmoc solid-phase peptide chemistry with a Prelude Parallel Peptide Synthesizer (Protein Technologies). The synthesized peptides were purified using a C18 reverse-phase column on an Agilent 1200 preparative HPLC system. Peptides were characterized using liquid-chromatography mass spectrometry (LC/MS) on an Accela/LTQ system (Thermo-Finnegan) and matrix-assisted laser desorption/ionization time-of-flight mass spectrometry (MALDI-TOF/TOF) on a Voyager 4800 instrument (Applied Biosystems).

In vitro kinase assay. Recombinant Abl, Src and Lyn enzymes were obtained from a commercial source (Millipore). EGFP-conjugated Syk was isolated from DT40 chicken B cells stably expressing Syk-EGFP. GFP-conjugated Lck was isolated from Jurkat cells stably expressing Lck-EGFP. Cells were lysed using a solution containing 1% Nonidet P-40, 50 mM Tris-HCl pH 8.0, 100 mM NaCl, 5 mM EDTA, 1 mM sodium orthovanadate, 2 mM NaF and 1× mammalian protease inhibitor cocktail (Sigma). Syk- and Lck-EGFP were immunoprecipitated using GFP-Trap_A beads (Chromotek) or anti-GFP magnetic nanoparticle beads (MBL, Japan). Lysates were incubated with the beads for 1 h at 4° C. The kinase-bound beads were washed and then used in the in vitro kinase assay. Syk-EGFP, Lck-EGFP, or purified Abl or Src kinase (0.1 U) were incubated with kinase reaction buffer (500 µM ATP, 5 mM $MnCl_2$, HEPES, pH 7.2) containing the peptide substrate at 25 µM. Aliquots (22 µL) were taken at designated time points and quenched in 0.5 M EDTA, pH 8.5 (22 µL). The quenched sample (1 µL) was diluted into ELISA-based detection wash buffer and analyzed as described below. For substrate comparison assays, kinase reaction conditions were as described above except that substrate concentrations were 4 µM, and concentration of enzyme used per reaction was 6 nM. The volume of aliquots diluted in an equal volume of quench buffer was 4 µl (for 8 µl total quenched volume), and the entire quenched amount was diluted into ELISA wash buffer and analyzed as described below.

ELISA-based fluorescence detection. Samples were incubated in a 96-well Neutravidin™ coated plate (Thermo Scientific) in Tris-buffered saline (TBS) containing 0.1% BSA and 0.05% Tween 20 for 1 h at room temperature on a short-radius plate shaker (600 rpm). Following incubation, wells were washed three times with wash buffer (TBS, 0.1% BSA, 0.05% Tween 20), then incubated with mouse anti-phosphotyrosine monoclonal antibody 4G10 (1:5000 dilution in wash buffer, 100 µL per well) for 1 h at room temperature with shaking. Wells were washed three times with wash buffer and incubated with horseradish peroxidase-conjugated goat anti-mouse immunoglobulin G (IgG) secondary antibody (Abcam) (1:1000 dilution in the wash buffer, 100 µL per well) for 1 h at room temperature with shaking. Wells were then washed three times with wash buffer and twice with sodium phosphate buffer (0.05 M, pH 7.5). For chemifluorescence detection, Amplex Red™ reaction buffer (100 µL total volume/well) consisting of Amplex Red™ reagent (50 µL) (Invitrogen), 20 mM $H_2O_2$ (500 µL) and sodium phosphate buffer (4500 µL) and allowed to react for 30 min. Fluorescence of Amplex Red™ was measure using a Synergy4 multiwell plate reader (Biotek) with an excitation wavelength of 532 nm and emission wavelength of 590 nm.

Peptide biosensor assay. Cells were cultured as described above, harvested and resuspended at a density of $8\times10^6$ cells/mL (8 mL), then treated with the Syk biosensor peptide (25 µM) for 15 min prior to stimulation with either anti-IgM antibody (5 µg/mL), $H_2O_2$ (3.33 mM) or both. Aliquots of the cell suspension (1 mL) were harvested, lysed in Phosph-Safe Extraction Reagent (EMD Millipore) containing 167 mM EDTA and freshly prepared protease inhibitor cocktail (Roche) and flash frozen. Half the cell lysate from each sample was used for ELISA-based fluorescence detection and the other for immunoblotting. For dose-response experiments, cells were stimulated with varying concentrations of anti-IgM (2.5-10 µg/mL) or hydrogen peroxide (1-7 mM), harvested at 5 min post-stimulation and processed as described above. For immunoblotting, membranes were blocked in 5% goat serum for 1 h. All primary antibodies were incubated at a dilution of 1:1,000 for 1 h at room temperature and visualized using an HRP-conjugated secondary antibody (Pierce) and ECL reagents (PerkinElmer).

Cell-Based peptide SAStide biosensor assay. Cells were cultured as described above, harvested and resuspended at a density of $8\times10^6$ cells/mL (8 mL), then treated with the SAStide biosensor peptide (25 µM) for 15 min prior to stimulation with either anti-IgM antibody (5 g/mL), $H_2O_2$ (3.33 mM) or both. Concentrations of peptide lower than 25 µM resulted in low signal to noise in detection of phosphopeptide using the ELISA-based read-out, and no toxicity was observed in the presence of the peptide at 25 µM (similar to what was observed in previously published work on Abl kinase). Aliquots of the cell suspension (1 mL) were harvested, lysed in PhosphoSafe Extraction Reagent (EMD Millipore) containing 167 mM EDTA and freshly prepared protease inhibitor cocktail (Roche) and flash frozen. Half the cell lysate from each sample was used for ELISA-based fluorescence detection and the other for immunoblotting. For dose-response experiments, cells were stimulated with varying concentrations of anti-IgM (2.5-10 µg/mL) or hydrogen peroxide (1-7 mM), harvested at 5 min post-stimulation and processed as described above. For immunoblotting, membranes were blocked in 5% goat serum for 1 h. All primary antibodies were incubated at a dilution of 1:1,000 for 1 h at room temperature and visualized using an HRP-conjugated secondary antibody (Pierce) and ECL reagents (PerkinElmer). Uniformity of the amount of peptide taken up was tested in a representative experiment using Syk-EGFP reconstituted Syk(−/−) DT40 cells, and while there was a very slight (but not statistically significant) trend towards higher peptide amounts over time, no significant difference was seen across conditions (see supporting information, FIG. S3).

Cell-based inhibition assay. Cells ($4\times10^6$ cells/ml) were pre-treated with varying concentrations of piceatannol or dasatinib for 30 min and with the Syk biosensor peptide (25 µM) for 15 min. Cells were then stimulated with anti-IgM antibody (5 µg/mL) and $H_2O_2$ (1 mM) and harvested after 5 min as described above.

Isolation of primary mouse splenic B-cells and primary cell biosensor assay. B cells were enriched from mouse spleens via panning. Cells 6 ml, $5\times10^6$ cells/mL) were treated with vehicle (DMSO), piceatannol (50 µM) or dasatinib (100 nM) for 1 h and with the Syk biosensor peptide (25 µM) for 15 min prior to stimulation. The cells were stimulated with anti-IgM F(ab')$_2$ (5 µg/mL). Cells were harvested at 0, 5, 10 and 15 min following stimulation, lysed and analyzed as described above.

Time-Resolved Luminescence Detection of Syk Kinase Activity Through Terbium Sensitization Luminescence Emission Measurements. Emission spectra (both steady-state and time-resolved) were collected on a Biotek Synergy4 plate reader equipped with a monochromator at 23° C. in black 384-well plates (Greiner Fluortrac 200). For time-resolved measurements, spectra were collected after excitation at either 266 nm or 280 nm (as denoted in specific experiments) with a Xenon flash lamp followed by a delay of 50 μsec. A luminescence scan between 450-650 nm was collected in 1 nm increments with 1 msec collection time and 10 readings per data point. Sensitivity (an instrument parameter similar to gain) was adjusted as necessary and is reported where relevant.

Job's Plot. The molar fraction of the pSAStide biosensor and $Tb^{3+}$ were continuously varied inversely of each other while maintaining a total molar concentration of 16 μM (i.e. 1 μM pSAStide and 15 μM $Tb^{3+}$, 2 μM pSAStide with 14 μM $Tb^{3+}$, . . . , 15 μM pSAStide and 1 μM $Tb^{3+}$) for each data point. Luminescent emission spectra were collected as described above and the area under the emission spectra was used as the parameter for quantification of complex formation as luminescent increases with complex formation.

Binding Affinity. $Tb^{3+}$ binding to SAStide and pSAStide was measured using $Tb^{3+}$ luminescence sensitized by the central tyrosine or phosphotyrosine residue of SAStide and pSAStide respectively. $Tb^{3+}$ was added to 100 nM of either peptide at final concentrations ranging from 0 to 20 μM. All experiments were carried out in 10 mM HEPES and 100 mM NaCl (pH 7.5) at a volume of 100 μL. After excitation of the samples at 266 nm (pSAStide) or 280 nm (SAStide), $Tb^{3+}$ luminescence emission spectra between 450 to 650 nm were collected for 1 ms following a 50 μs delay and 30 readings per data point. Background luminescence emission was subtracted from the peptide in the absence of terbium. The area under each spectrum was integrated and used as the metric for quantification. The data were fit to Eq. 1 by using KaleidaGraph nonlinear curve-fitting software, where I is the $Tb^{3+}$ luminescence at a given concentration, $I_{max}$ corresponds to the maximum $Tb^{3+}$ emission, $[Tb^{3+}]_T$ is the total $Tb^{3+}$ concentration, $[P]_T$ is the total peptide concentration and $K_d$ is the equilibrium dissociation constant.

$$I = I_m*([Tb^{3+}]_T + K_d + [P]_T) - \sqrt{(([Tb^{3+}]_T + K_d + [P]_T)^2 - 4([Tb^{3+}]_T*[P]_T))/(2*[P]_T)} \quad (1)$$

In vitro kinase assay. EGFP-conjugated Syk was isolated from DT40 chicken B cells stably expressing Syk-EGFP. Cells were lysed using a solution containing 1% Nonidet P-40, 50 mM Tris-HCl pH 8.0, 100 mM NaCl, 5 mM EDTA, 1 mM sodium orthovanadate, 2 mM NaF and 1× mammalian protease inhibitor cocktail (Sigma). Syk-EGFP was immunoprecipitated using GFP-Trap_A beads (Chromotek). Lysates were incubated with the beads for 1 h at 4° C. The kinase-bound beads were washed and then used in the in vitro kinase assay (0.4 μg/μL). Syk-EGFP was incubated with the kinase reaction buffer (3.4 μg Syk-EGFP, 100 μM ATP, 10 mM $MgCl_2$, 1 μM $Na_3VO_4$, leupeptin, aprotinin, 125 ng/μL BSA and 25 mM HEPES pH 7.5, total volume 170 μL) containing SAStide at 37.5 μM at 30° C. Aliquots (20 μL) were taken at designated time points (0.5, 5, 10, 15, 30, 45, 60 and 90 min) and quenched in 6 M urea (20 μL). The quenched samples were then treated with the luminescence buffer (500 μM $Tb^{3+}$ and 500 mM NaCl, 10 μL) for a total volume of 50 μL (final concentrations of sample components: 2.4 M urea, 40 μM ATP, 4 mM $MgCl_2$, 0.4 μM $Na_3VO_4$, leupeptin, aprotinin, 50 ng/μL BSA and 10 mM HEPES pH 7.5). Luminescence emission spectra were collected as described above and the area under each spectrum was integrated using GraphPad Prism. An additional aliquot (1 μL) of the kinase reaction mixture was taken at each time point for validation of phosphorylation using an ELISA-based chemifluorescent assay. Briefly, each aliquot was quenched with 0.5 M EDTA and incubated in a 96-well Neutravidin coated plate (15 pmol biotin binding capacity per well, Thermo Scientific) in Tris-buffer saline (TBS) containing 0.1% BSA and 0.05% Tween 20 for 1 h. Following incubation, each well was washed with the TBS buffer and the incubated with mouse anti-phosphotyrosine monoclonal antibody 4G10 (Millipore, 1:10,000 dilution in TBS buffer) for 1 h. Following incubation, each well was washed with TBS buffer and incubated with horseradish peroxidase-conjugated goat anti-mouse immunoglobulin G (IgG) secondary antibody (Abcam) (1:1000 dilution) for 1 h. Wells were then washed and treated with Amplex Red reaction buffer (Amplex Red reagent, Invitrogen, 20 mM $H_2O_2$ and sodium phosphate buffer) for 30 min. Fluorescence was measured using a Synergy4 multiwell plate reader (Biotek) with an excitation wavelength of 532 nm and emission wavelength of 590 nm.

Dose-Response Inhibition Assay. Syk-EGFP (0.4 μg/reaction) was incubated with the kinase reaction buffer described above before adding SAStide in the presence of DMSO (vehicle) or varying concentrations of piceatannol at 30° C. for 10 min prior to the start of the reaction. The reaction was started with the addition of SAStide (37.5 μM, total reaction volume 20 μL). Each reaction was quenched after 30 min in 6 M urea (20 μL). The samples were then treated with the luminescence buffer (500 μM $Tb^{3+}$ and 500 mM NaCl, 10 μL) for a total volume of 50 μL.

High-Throughput Screening Calculations. The Z' factor was calculated according to Eq. 2.

$$z' = (\mu_{pos} - 3\sigma_{pos}/\sqrt{n}) - (\mu_{neg} + 3\sigma_{neg}/\sqrt{n})/(\mu_{pos} - \mu_{neg}) \quad (2)$$

And the signal window was calculated according to Eq. 3

$$SW = (\mu_{pos} - 3\sigma_{pos}/\sqrt{n}) - (\mu_{neg} + 3\sigma_{neg}/\sqrt{n})/(\sigma_{pos}/\sqrt{n}) \quad (3)$$

Where n is the number of replicates, $\mu_{pos}$ and $\mu_{neg}$ are the average luminescence of the positive (pSAStide or uninhibited) and negative (SAStide or inhibitor treated EGFP-Syk) controls respectively; $\sigma_{pos}$ and $\sigma_{neg}$ are the standard deviation of the positive and negative controls.

Strategy and Method to Facilitate Identification of Kinase Substrate Sequences Substrate Informatics Predicting kinase substrate specificity is a binary classification problem as each sequence can be classified as phosphorylated (substrate) or non-phosphorylated (non-substrate). Establishing a method for predicting of kinase substrate specificity requires having a well collected and curated data set of positive and negative sequences, identification of features to characterize the sequences as one of the two classes, and the development of a classifier trained from the known sequences capable of making the prediction for new sequences.

In this study, for each kinase, an individual prediction model was trained from a collection of non-redundant phosphorylated sequences. Output from positional probabilities and positional scanning peptide libraries (PSPL) were taken as features to generate a positional scoring matrix (PSM) for each kinase and the PSM score was used as the classifier. The prediction model was then trained using the collection of substrates and non-substrate sequence collected through n-fold cross validation.

Data Collection and Construction.

In this study, substrates for each kinase were gathered from the literature as well as phosphorylation site repositories including Phosphosite Plus, Phospho.ELM and the Human Protein Reference Database. Negative substrates derived from the proteins containing substrate sequences and interacting proteins containing no substrate sequences. Additionally, a PSPL was used to determine empirical effects of each amino acid on the catalytic efficiency of the kinase towards the substrate sequence.

Feature Extraction.

Positional Probability— Generally, there is a pattern in the regions surrounding the phosphosite that a specific kinase phosphorylates. To identify features to characterize the two classes, substrate sequence alignment can be analyzed to identify redundant properties of various amino acid side chains. The development of a matrix can display the observed frequencies compared to the expected frequencies. These PSM matrices can be used to generate a score for a given kinase and a substrate. The higher the score the more likely the kinase is to phosphorylate the substrate. To characterize a sequence nine amino acids, four amino acids on either side of the phosphorylation site were considered in the score. These positions were chosen based on the disorder in substrates. The probability matrix, PM, was calculated as follows. It is experimentally known that kinase k phosphorylates n substrates $(n_1, n_2, \ldots, n_n)$ consisting of nine amino acids, four on each side of the phosphorylation site. The frequency of each amino acid at each position in the collection of substrates was computed, $f_{j,i}$, where j is amino acid (A, C, ..., W, Y) at position i (−4, −3, ..., 1). Due to the limitation of identified substrates for some kinases, when j=0 for those amino acids the value of j=1/n, where n is the number of substrate sequences for kinase k. The matrix values were computed by comparing the observed frequency, $f_{i,j}$, within the substrates to the expected frequency (background frequency), $b_{i,j}$, derived from the frequency of each amino acid in each protein containing a substrate sequence as well as non-phosphorylated interacting proteins. This allowed for the background of amino acids to reflect what kinase naturally interacts. A probability matrix 20×9 was constructed for each amino acid and position defined as $s_{i,j}=f_{i,j}/b_{i,j}$.

Positional Scanning Peptide Library— The positional scanning peptide library has been previously reported. For each array, peptide phosphorylation signals were quantified based on the median intensity for each spot. The median intensity values were then background corrected and signal intensity were then normalized by the following equation:

$$Z_{ij}=m \times (S_{ij}/\Sigma S_{ci})$$

where $Z_{ij}$ stands for the normalized score of amino acid j at position i having a signal score $S_{ij}$ and m stand for the total number of amino acids. $S_{ci}$ is the signal score of amino acid j at position i where i is defined in the summation of all the m amino acids.

Positional Scoring Matrix—The two individual matrices, PM and PSPLM, were multiplied to form the positional scoring matrix, PSM. The value for each amino acid can then be used to identify favorable and unfavorable residues at each position. Values greater than 0.9 were considered favorable or permissive for the kinase, while values less than 0.9 were consider unfavorable or impermissive.

For an nonapeptide of a given amino acid sequence the product of all $s_{i,j}$ values yields the raw probability score, $S_R$.

$$S_R = \Pi^8_{i=1} s_{i,j}$$

The raw score was normalized by probability of any nonapeptide being a substrate for kinase k, $P_s$. $P_s$ was determined by the number kinase substrates collected n plus the number of significantly peptides from the PSPL compared to the total number tyrosine center nonpeptides seen in substrate and interacting proteins and the 200 peptides from the PSPL for kinase k.

$$P_s=(n+x)/(n_T+200)$$

$$S=S_R/(S_R+1/P_S)$$

Positional selectivity, $S_i$, was determined by the ratio of the number of significantly abundant residues found at the subsite, $n^{sig}_{i,j}$, compared to the expected abundance from a random distribution, $n^{sigaa}_{i,j}$, multiplied by the ratio of the number significantly abundant at the subsite to the total number of residues, $n^{aa}_{i,j}$.

$$S_i([\Sigma_j n^{sig}_{i,j}/\Sigma_j n^{sigaa}_{i,j}] \times [\Sigma_j n^{sig}_{i,j}/\Sigma_j n^{aa}_{i,j}])$$

An amino acid was defined as being significantly abundant if its frequency was found to be greater than two standard deviations above the mean. This selectivity can be used to identify the selectivity of given sites within the substrate for a given kinase. If a site is nonselective, the properties of the site can be tuned to allow for specificity against other kinases or to allow for terbium binding. More selective sites should only consider the best residues for the design of the substrate.

Performance Evaluation. To evaluate the prediction performance of the algorithm, receiver operating characteristic (ROC) curves were calculated and plotted based on the specificities (Sp) and sensitivities (Sn) by taking different thresholds.

Specificity(Sp)=TN/TN+FP

Sensitivity(Sn)=TP/TP+FN where, TP is the number of true positive predictions (phosphorylation predictions in the positive data set), TN is the number of true negative predictions (non-phosphorylated predictions in the negative data set), FN is the number of false negative (non-phosphorylated predictions in the positive data set), and FP is the number of false positives (phosphorylation predictions in the negative data set). Areas under ROC curves (AROC) were also calculated based on the integration and used as the Mann-Whitney U statistic.

Additional characterization was performed by the following:

Accuracy(Ac)=(TP+TN)/(TP+FN+TN+FP)

Precision(Pr)=TP/(TP+FP)

Equal Error Rate(EER)=(1−Sn)*(TP+FN)+((1−Sp)* (1−(TP+FN)))*0.01

Matthews Correlation Coefficient(MCC)=((TP×TN)− (FP×FN))/√(TP+FP)(TP+FN)(TN+FP)(TN+FN)

Generation of Kinase Focused Peptide Libraries. Kinase focused peptide libraries were generated based on the values of the PSM. All $s_{i,j}>0.9$ were chosen as potential residues at each position. Combinatorial peptide sequences were generated from these residues and scored against each kinase. Those peptides that scored positive for the kinase of interest and negative for all other kinases were then selected for further screening.

Terbium Binding Screening. Following the generation of the focused kinase library sequences were screened for the ability to bind terbium in a phosphorylation-dependent manner. A BLOSUM 62 matrix was used to generate a sequence similarity score between the focus library of potential kinase substrates and known terbium sensitizing substrate such as α-syn Y125 (DPDNEAYEMPSEEG) (SEQ ID NO:33) and SAStide (GGDEEDYEEPDEPGG) (SEQ ID NO:12)

Terbium based in vitro kinase assays. Recombinant kinases were incubated with the kinase reaction buffer (15 nM kinase, 100 μM ATP, 10 mM MgCl$_2$, 125 ng/μL BSA and 25 mM HEPES pH 7.5, total volume 180 μL) containing 12.5 μM biosensor at 30° C. Aliquots (20 μL) were taken at designated time points (0.5, 5, 10, 15, 30, 45 and 60 min) and quenched in 6 M urea (20 µL). The quenched samples were then treated with the luminescence buffer (500 µM Tb$^{3+}$ and 500 mM NaCl, 10 µL) for a total volume of 50 µL (final concentrations of sample components: 2.4 M urea, 40 µM ATP, 4 mM MgCl$_2$, 50 ng/µL BSA and 10 mM HEPES pH 7.5). Luminescence emission spectra were collected as described above and the area under each spectrum was integrated using GraphPad Prism. An additional aliquot (2 µL) of the kinase reaction mixture was taken at each time point for validation of phosphorylation using an ELISA-based chemifluorescent assay as previously described. Briefly, each aliquot was quenched with 0.5 M EDTA and incubated in a 96-well Neutravidin coated plate (15 pmol biotin binding capacity per well, Thermo Scientific) in Tris-buffer saline (TBS) containing 0.1% BSA and 0.05% Tween 20 for 1 h. Following incubation, each well was washed with the TBS buffer and the incubated with mouse anti-phosphotyrosine monoclonal antibody 4G10 (Millipore, 1:10,000 dilution in TBS buffer) for 1 h. Following incubation, each well was washed with TBS buffer and incubated with horseradish peroxidase-conjugated goat anti-mouse immunoglobulin G (IgG) secondary antibody (Abcam) (1:1000 dilution) for 1 h. Wells were then washed and treated with Amplex Red reaction buffer (Amplex Red reagent, Invitrogen, 20 mM H$_2$O$_2$ and sodium phosphate buffer) for 30 min. Fluorescence was measured using a Synergy4 multiwell plate reader (Biotek) with an excitation wavelength of 532 nm and emission wavelength of 590 nm.

Dose-response Inhibition Assay. Kinase (15 nM) was incubated with the kinase reaction buffer described above before adding SAStide in the presence of DMSO (vehicle) or varying concentrations of kinase inhibitors (nilotinib, bosutinib, ruxolitinib) at 30° C. for 10 min prior to the start of the reaction. The reaction was started with the addition of biosensor (12.5 µM, total reaction volume 20 µL). Each reaction was quenched after 30 min in 6 M urea (20 µL). The samples were then treated with the luminescence buffer (500 µM Tb$^{3+}$ and 500 mM NaCl, 10 µL) for a total volume of 50 µL.

High-Throughput Screening Calculations. The Z' factor was calculated according to Eq. 2.

$$Z'=(\mu_{pos}-3\sigma_{pos}/\sqrt{n})-(\mu_{neg}+3\sigma_{neg}/\sqrt{n})/(\mu_{pos}-\mu_{neg}) \quad [2]$$

And the signal window was calculated according to Eq. 3

$$SW=(\mu_{pos}-3\sigma_{pos}/\sqrt{n})-(\mu_{neg}+3\sigma_{neg}/\sqrt{n})/(\sigma_{pos}/\sqrt{n}) \quad [3]$$

Where n is the number of replicates, $\mu_{pos}$ and $\mu_{neg}$ are the average luminescence of the positive (phosphorylated peptide or uninhibited) and negative (unphosphorylated peptide or inhibitor treated) controls respectively; $\sigma_{pos}$ and $\sigma_{neg}$ are the standard deviation of the positive and negative controls.

Detection of Bcl-Abl Kinase Activity
Cell-based Biosensor Assay for Multiple Reaction Monitoring to Detect Bcr-Abl.

Three independent replicate experiments were performed for the time course with Western blot detection. Three side-by-side replicate experiments with just one time point (5 min) were performed for the MRM analysis. K562 cells were cultured to log phase growth and seeded to 5×10$^6$ cells/ml in a six-well plate (3 mL per well). When necessary, cells were pre-incubated with imatinib (10 µM) for 1 h at 37° C. followed by incubation with three treatments: 25 µM peptide (dissolved in PBS), 25 µM peptide+10 µM imatinib, and 25 µM peptide+1 µM pervanadate (prepared by reacting a solution of sodium orthovanadate with H$_2$O$_2$, followed by heating at 95° C. to degrade excess H$_2$O$_2$). At the indicated time points (5, 30, 60 min), aliquots (1 mL) were collected and centrifuged (2200 rcf, 1 min, 4° C.) to remove excess media. To collect any remaining cells in the wells from the final aliquot, all wells were washed with phosphate buffered saline (PBS, 400 µl) and these washes were combined with the collected cells. Cells were suspended in PBS (1 ml) to wash away excess peptide, centrifuged again (2200 rcf, 1 min, 4° C.), and lysed using Phosphosafe Extraction Reagent (Novagen) supplemented with EDTA and protease inhibitor cocktail (Roche). Cells were immediately flash-frozen in liquid nitrogen, thawed on ice for 15 min, vortex mixed, and centrifuged to clarify (16,000 rcf, 15 min, 4° C.). The supernatant was collected, measured for total protein concentration using the BCA assay (ThermoFisher Pierce, Rockford, Ill.), flash frozen again and stored at −80° C. until use.

Enrichment and MALDI-TOF/TOF Analysis.

Biosensor peptide from samples generated as described above (in the cell-based biosensor assay section) was captured using streptavidin-coated MagneSpheres (Promega Corporation, Madison, Wis.). The beads (20 µl) were prepared by washing with 0.1% Octyl-j-glucoside/PBS (3×150 µl). K562 cell lysates (200 µg total protein) were incubated with the beads on a shaker (600 rpm, 60 min). Beads were captured using a MagnaBot 96-well magnetic capture device (Promega) and washed with 0.1% Octyl-(3-glucoside/PBS (3×150 µl) and deionized water (3×150 µl). Peptide was eluted using 15 µL sample buffer (ACN/H2O/TFA, 50%/50%/0.1%). 0.5 µL from each sample was co-spotted with α-cyano-4-hydroxycinnamic acid (10% w/v) containing ammonium dihydrogen phosphate (5 mg/ml), dried and analyzed on a 4800 MALDI-TOF/TOF Analyzer (ABSciex). Selected ions were analyzed by MS/MS (specifying the parent ion mass for selection and CID) and sequenced de novo.

Western blot analysis. Samples of equal protein content (100 µg/lane) were diluted into Laemmli buffer and subjected to SDS-PAGE. Proteins were transferred to nitrocellulose membrane and analyzed by Western blotting. Membranes were split at the 15 kD mark and blocked in 3% milk in TBS-T overnight at 4° C., followed by blotting with the indicated antibodies in 3% milk/TBS-T. The bottom membrane was blotted with: DyLight-649 labeled Streptavidin (1:1000, ThermoFisher Pierce) to detect total biosensor; 4G10 α-phosphotyrosine antibody to detect the phosphorylated biosensor. Upper section of the membrane was blotted with: α-phospho-Abl (Y245) (1:1000, Cell Signaling), α-phospho-STAT5 (Y694) (1:5000, Abcam) and α-phospho-CrkL (Y207) (1:1000, Abcam) to detect phosphorylation of endogenous sites in the Bcr-Abl signaling pathway. α-β-tubulin (1:100,000, Millipore) was used as a loading control. Blots were incubated with IR-dye-labeled secondary antibodies (Rockland Immunochemical) in 3% milk/TBS-T (1:10,000). Signals of immunoblots were visualized using the Odyssey system (LiCOR Biosciences, Lincoln, Nebr.), quantified using densitometry with Quantity One (Bio-Rad), and analyzed with GraphPad Prism software.

Sample Preparation and Digestion

Aliquots (18 µg each) of cell lysate samples were processed to separate proteins from lipids. Chloroform/methanol/water (2:2:1.8 v/v/v) was added to the samples and the mixture vortex mixed, followed by centrifugation (5 min at 3000 rpm) to separate the chloroform and aqueous layers. The aqueous layer was retained and extracted again in the same manner, after which the chloroform layers containing lipids were discarded. The extracted protein in the aqueous layer was then precipitated with cold acetone prior to the digestion protocol, in which the samples were taken up in ammonium bicarbonate buffer (50 mM) containing 0.1% (w/v) RapiGest SF (Waters Corporation, Milford, Mass.) to give protein concentrations of 1 µg/l. Dithiothreitol (DTT, 10 mM) was added (1:1 per volume, for a final concentration of 5 mM) and the sample incubated at 60° C. for 30 min to denature the proteins. After cooling to room temperature, samples were incubated in the dark with iodoacetamide (final concentration 15 mM from 55 mM stock) for 30 min. Trypsin was added (0.5 µg) and the samples incubated at 37° C. for 18 h. Following digestion, samples were treated with TFA (10% stock to give final concentration 0.2% w/v) at 37° C. for 30 min. Samples were diluted with 0.01% TFA to 0.5 µg/dl, centrifuged to clarify, and the supernatant injected directly onto the triple quadrupole LC/MS system (described below) for analysis (2 µl per sample, for a total protein loading of ~1 µg). For calibration standards, Abl biosensor peptide and synthetic reporter segment were added into lysate at appropriate concentrations to result in 5-250 fmol per 2 p injection, then digested and prepared as described above.

LC-MS/MS Analysis

Tryptic peptides were separated on a nano-LC/MS system which included Agilent 1100 Series capillary and nano flow pumps, micro-well plate sampler with thermostat, and Chip Cube MS interface on the Agilent 6410 Triple Quadrupole mass spectrometer (Agilent Technologies, Santa Clara, Calif.). The peptides were loaded at 3 µl/min on an Agilent chip containing a 40 nl enrichment column packed with Zorbax 300SB-C18 5 µm material. The enrichment column was switched into the nano flow path after 5 min, and peptides were separated with an analytical column (0.75 µm×150 mm) packed with C18 reverse phase ZORBAX 300SB-C18 5 µm material at a flow rate of 0.3 µl/min. The chip is coupled to the electrospray ionization (ESI) source of the triple quadrupole mass spectrometer. The peptides were eluted from the column using a linear gradient of increasing acetonitrile. For the first 5 min, the column was equilibrated with 5% acetonitrile/95% water/0.1% formic acid (mobile phase A) followed by a linear gradient of 5%-15% B (100% acetonitrile/0.1% formic acid) in 10 min, 15-22% B in 30 min, and 22-100% B in 35 min. The column was washed with 100% B and then equilibrated with A before the next sample was injected. Blank injections were run between samples to avoid carryover.

Product ion scans were run on the triple quadrupole instrument and analyzed using Skyline software (MacCoss Labs, WA) to develop a method to monitor transitions from each peptide of interest. Quadrupole 1 and 3 were run at unit resolution with a minimum dwell time of 30 msec. Using this method, peptides of interest were analyzed by multiple reaction monitoring mass spectrometry (MRM-MS). Standard peptides were synthesized and diluted into stock solutions in deionized water (using dry weight as measured by analytical microbalance) and concentration curves (in fmol) were used for quantitation of the peptides in the cell lysate samples.

Results

For initial design of Syk substrates, expected frequencies were calculated from the occurrence of each amino acid in the phosphorylation site-containing proteins, in order to normalize to the representation of each amino acid in all substrate proteins. An amino acid or property was considered "significantly abundant" at positions in a tyrosine-surrounding sequence if its frequency was two standard deviations greater than the mean frequency of that amino acid anywhere in the set of substrate proteins. "Selectivity scores" were then assigned to each site based on the abundance of significant amino acids and the properties observed at each site. The selectivity score for each of the positions surrounding the tyrosine (−4 to +4) was calculated based on how over-represented the significantly abundant amino acids were at a site compared to their expected frequencies. The higher the selectivity score, the more "selective" the kinase was for that site (in other words, the more the kinase preferred a certain amino acid at that site), while scores closer to one indicate marginal preference for that site by the kinase.

Syk was observed to showed high selectivity at the −4 to +3 subsites of Syk substrates, while the +4 position demonstrated no selectivity. Syk favors acidic residues at all the upstream sites as well as the +1 and +2 positions. In addition, some preference for asparagine at the −2 and +2 positions and valine at the +1 position were also identified. Finally, the +3 position displayed a preference for the amino acids valine and proline. Using this information for preferences at a given position, a Syk peptide substrate, DEEDYEEPDEP (SEQ ID NO:2), designated SAStide, was developed. SAStide was incorporated with other functional modules to form a Syk biosensor peptide. These modules may include a tag for affinity capture of the substrate, a cell penetrating peptide for delivery of the biosensor into cells, and a cleavable linker, such as a photocleavable amino acid, for release of the substrate from the rest of the biosensor to permit mass spectrometry-based analysis. In one embodiment, the Syk biosensor has the sequence GGDEEDYEEP-DEPGGKbiotinGG-βNpa-RKKRRQRRR (SEQ ID NO:34), with a biotinylated lysine ($K_{biotin}$) for affinity capture of the substrate, the cell penetrating peptide RKKRRQRRR (SEQ ID NO:35), and the photocleavable amino acid beta(nitrophenyl)alanine or βNpa, also known as 3-(2-nitrophenyl)-3-aminopropionic acid.

Phosphorylation of SAStide by Syk In Vitro

Phosphorylation of the biosensor by Syk was assessed using an in vitro kinase assay. In control experiments to generate a standard curve, phosphorylated SAStide was demonstrated to bind reproducibly to the wells, and exhibited a linear increase in signal up to an amount of phosphopeptide per well of 0.5 pmol, beyond which saturation of the ELISA signal occurred. This validated that the amount of antiphosphotyrosine antibody-related signal was proportionally related to the degree of peptide phosphorylation. A substantial increase in signal over time was observed, demonstrating that SAStide was phosphorylated by Syk in vitro. SAStide was also assayed using Src, Abl and Lyn kinases, none of which produced any significant signal for phosphopeptide.

Detection of Dose Dependent Activation and Inhibition of Syk in Intact Cells.

The ability of the biosensor to detect dose-dependent activation of Syk in the context of BCR activation by anti-IgM and $H_2O_2$-induced oxidative stress in intact, living Burkitt's lymphoma DG75 B-cells was examined. Syk activity was analyzed after 5 min and compared to unstimulated cells as a control. No signal above the reagent background was observed in cells not treated with the peptide. BCR activation by anti-IgM resulted in increased phosphorylation of the biosensor in a dose-dependent manner. Induction of oxidative stress in the B cells by hydrogen peroxide treatment also resulted in dose-dependent increases in phosphorylation of the biosensor. These results show the ability of the peptide biosensor to detect dose-dependent changes in the Syk activity at endogenous levels of expression in live cells.

The ability of the biosensor to monitor dose-dependent inhibition of Syk using the Syk-specific natural product inhibitor piceatannol and the Src-family kinase inhibitor, dasatinib, a potential therapeutic Syk inhibitor, was examined. The inhibitors were assayed in a dilution series from 1 mM-100 pM. Dasatinib was found to have a greater potency than piceatannol in inhibiting Syk phosphorylation of the biosensor. However, high concentrations of piceatannol in the presence of BCR activation and oxidative stress were toxic to DG75 cells whereas dasatinib was not. The apparent $IC_{50}$ values, the concentration at which SAStide phosphorylation was decreased by 50% compared to the control uninhibited cells, were calculated using the Hill function to be 10.8±9.3 nM and 1.2±1.5 µM for dasatinib and piceatannol, respectively. These results are consistent with a reduction in the level of Syk tyrosine phosphorylation as detected by Western blot analysis.

Time-dependence of Syk Activity Following Activation.

To examine the time dependence of Syk activity following stimulation through BCR and/or oxidative stress, DG75 cells were treated as above and Syk biosensor phosphorylation was analyzed every few minutes for the first 15 min following stimulation. BCR stimulation gave a rapid increase followed by steadily maintained phosphorylation of the biosensor. As expected, the addition of hydrogen peroxide following BCR stimulation gave a very robust increase in phosphorylation over the time course due to the amplified and extended BCR signaling. Oxidative stress alone also resulted in increased phosphorylation of the biosensor, peaking at 5 min and subsequently showing a slight decrease. These results demonstrate that the SAStide biosensor is able to monitor time-dependent increases in Syk activity in live cells following stimulation.

Determination of the SAStide Biosensor Specificity in Intact Cells

Selective phosphorylation of the SAStide biosensor was evaluated in the context of the complex intracellular environment. The specificity of the biosensor as a substrate for Syk and not other tyrosine kinases in live cells was explored using DT40 chicken B-cells in which the endogenous gene for Syk has been eliminated by homologous gene targeting. No significant change in phosphorylation of the biosensor was detected over the time course following stimulation when compared to unstimulated control cells. These results indicate that the specificity of the biosensor was maintained in living cells in the context of IgM engagement and BCR-activated signaling.

Hydrogen peroxide was added to amplify BCR-stimulated phosphorylation. As seen with the anti-IgM stimulation alone, no significant change in the phosphorylation of the biosensor was detected over unstimulated cells. Western blot analysis of tyrosine-phosphorylated proteins demonstrated amplified phosphotyrosine signaling compared to anti-IgM treatment alone, indicating activation of multiple tyrosine kinases and inhibition of tyrosine phosphatases. No significant change in the phosphorylation of the biosensor was detected in cells treated only with hydrogen peroxide. These results show that even in the presence of amplified and extended BCR-related and other $H_2O_2$-related signaling, the SAStide biosensor was not appreciably phosphorylated by other highly activated tyrosine kinases in Syk-deficient cells. This experiment serves as a highly relevant specificity control in the intracellular context, given that tyrosine kinase activity was dearly upregulated, yet none of these activated kinases phosphorylated the biosensor peptide.

The same set of experiments was conducted in Syk (−/−) DT40 cells that had been reconstituted with Syk-EGFP. In the presence of BCR stimulation by IgM, phosphorylation of the biosensor peptide increased approximately 2-fold over unstimulated Syk-EGFP-expressing cells and decreased slightly over time. When treated with $H_2O_2$ with or without concurrent BCR stimulation, biosensor phosphorylation signal increased more dramatically to approximately 12-fold over control. Phosphorylation of the biosensor was consistent with that observed by Western blot analysis for the Syk autophosphorylation site and the known Syk substrate BLNK.

Detection of Syk Activity and Inhibition in Primary Mouse Splenic B-cells.

The ability of the biosensor to monitor Syk activity and response to inhibitor treatment in primary cells expressing endogenous levels of Syk was examined in isolated mouse primary splenic B cells treated with the biosensor peptide in the presence of piceatannol or dasatinib. Primary B cells were treated with 10 nM dasatinib, 1 µM piceatannol or vehicle (DMSO) for one h prior to stimulation. The SAStide biosensor peptide was added 15 min prior to stimulation. The cells were stimulated by treatment with anti-IgM F(ab')$_2$ (5 µg/mL) and harvested 0, 5, 10 and 15 min following stimulation. Stimulation of Syk activity following BCR engagement resulted in a rapid increase in phosphorylation of the SAStide biosensor (within approximately two minutes—the time required to handle and process an aliquot of cells collected immediately after stimulation) followed by a maintenance of phosphorylation over time as compared to control unstimulated cells, which showed only background levels of phosphorylation-related signal. In the presence of each inhibitor, the level of phosphorylation of the biosensor was decreased, giving a signal that was close to background levels. These results show that the biosensor peptide is capable of detecting activation and inhibition of endogenous Syk kinase expressed at normal levels in primary cells that exhibit physiologically relevant B cell receptor signaling, and suggest that elevation of Syk activity is very rapid in response to B cell receptor engagement in these primary cells.

Time-Resolved Luminescence Measurements Increase Signal to Noise.

Based on the similarity of the arrangement of carboxylate groups about the central tyrosine residue in SAStide and the motif found in α-synuclein, the atypical phosphorylation dependent terbium sensitizing peptide (FIG. 1A), the use of SAStide as a probe for the detection of Syk activity through terbium-sensitized luminescence was investigated.

Figure 2:
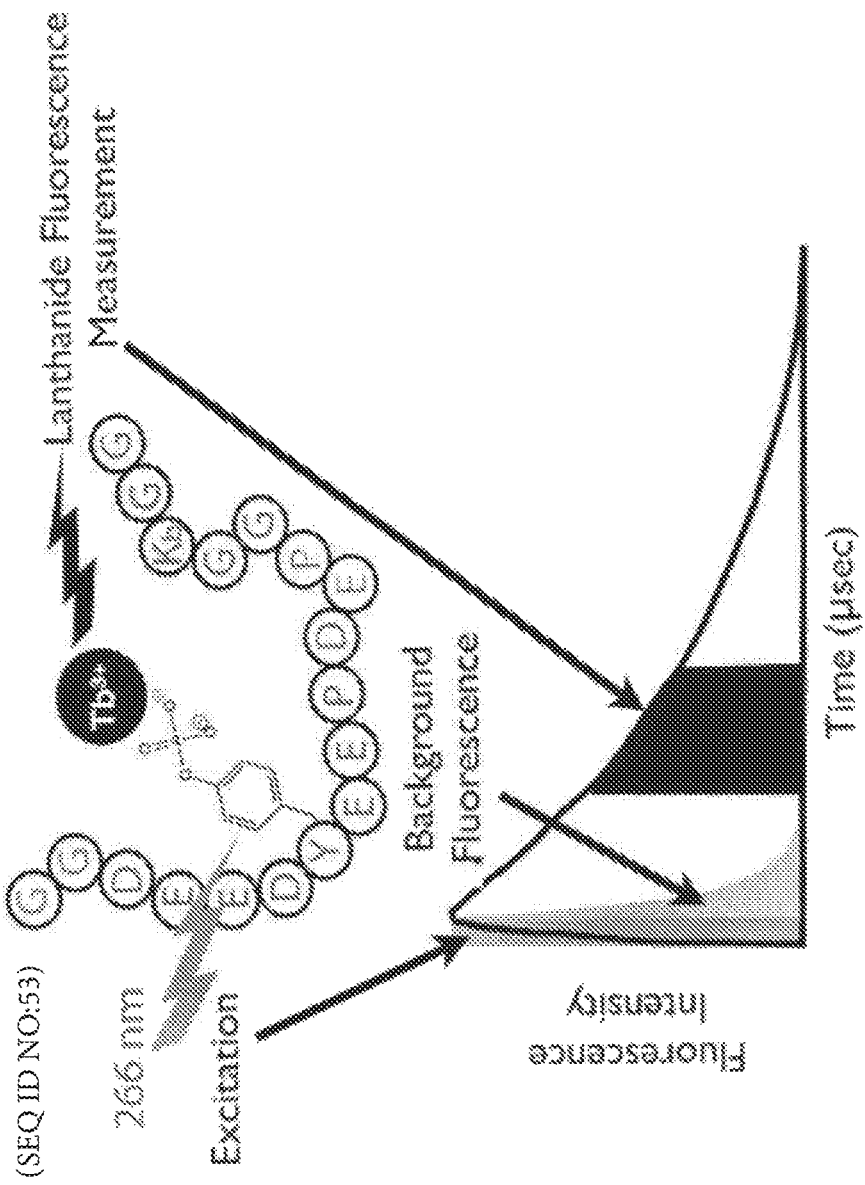
FIG. 2 is a schematic representation illustrating the concept of time-resolved luminescence in the detection of Syk activity using SAStide.

Phosphorylated (pSAStide) and unphosphorylated (SAStide) forms of the peptide were synthesized and steady-state luminescence of each 1:1 $Tb^{3+}$ complex with excitation at 266 nm through a monochromator (for highly resolved excitation energy control) was measured (FIG. 1B). The optimal excitation energy was determined to be 266 nm for pSAStide and 275 nm for SAStide and were used for characterizing each species in complex with terbium. At 266 nm excitation energy, pSAStide exhibited strong $Tb^{3+}$ sensitization and SAStide displayed weaker luminescence. Therefore, 266 nm was used for all further analyses. While signal from SAStide was somewhat mitigated by using 266 nm excitation energy, there was still weak but significant luminescence from SAStide so the signal to noise (comparing pSAStide and SAStide luminescence) was relatively low (2:1). It was therefore decided to test whether chelation of $Tb^{3+}$ with the phosphorylated vs. unphosphorylated peptide could be more easily distinguished using time-resolved luminescence detection. In a time-resolved luminescence measurement, the short-lived background luminescence is allowed to decay before measuring the luminescence of the chelated $Tb^{3+}$ (FIG. 2). Time-resolved luminescence was performed by collecting spectra from 15 μM peptide in the presence of 100 μM $Tb^{3+}$ in 10 mM HEPES, 100 mM NaCl, pH 7.0, $\lambda_{ex}$=266 nm, 1000 ms collection time, 50 μsec delay time and sensitivity 180. Time-resolved measurements significantly improved the signal to noise to 32:1 (FIG. 1C), demonstrating that taking advantage of the increase in $Tb^{3+}$ luminescence lifetime in the presence of phosphotyrosine vs. unphosphorylated tyrosine improved the ability to detect phosphorylation of SAStide. The improvement in the signal to noise ratio was accomplished by allowing the short-lived signal of the unphosphorylated peptide to decay prior to collection.

Physical Characterization of SAStide-Lanthanide Binding and Luminescence.

Binding studies were performed to determine the stoichiometry and affinity of pSAStide-terbium complexation. The binding stoichiometry of the highest affinity complex was established using the Jobs method of continuous variations. The area under the emission spectrum was used as the metric to quantify the pSAStide-$Tb^{3+}$ binding ratios. pSAStide and terbium individually displayed no detectable luminescence; therefore, any changes in luminescence could then be attributed the formation of the pSAStide-$Tb^3$ complex. The Jobs plot displayed an increase in total area as the mole fraction of terbium increased to 0.5 followed by a linear decrease with further increases in the mole fraction. These data indicated that the preferred binding stoichiometry of pSAStide-$Tb^{3+}$ binding is 1:1.

Binding affinities were also determined using $Tb^{3+}$ luminescence as a measure of complexation. Terbium was titrated in the presence of 100 nM pSAStide or SAStide and luminescence emission spectra were collected and integrated. The binding curves displayed a hyperbolic increase in luminescence with increasing terbium concentrations from 0-20 μM (representing a large excess of terbium), with saturation between at 20 μM characteristic of one site binding. Additional increases in luminescence, ranging up to three fold, were observed with increasing terbium concentrations, which mass spectrometry analysis suggested were likely due to complexes containing multiple terbium ions. However, for the remainder of this work detection of pSAStide was carried out with 6.67 equivalents of terbium relative to peptide, thus the 1:1 binding mode characterized by the initial hyperbolic increase was the most relevant to detection under conditions used subsequently for assays. The calculated $K_d$ for the 1:1 pSAStide-terbium complex represented by the hyperbolic curve was 1.51±0.087 M, which is comparable to the affinities reported for other terbium binding peptides. The unphosphorylated SAStide-terbium complexation displayed significantly weaker binding; the 1:1 complex exhibited a $K_d$ of 7.64±0.32 μM (5-fold weaker than for the phosphorylated peptide). These results demonstrate that phosphorylation increased the affinity of SAStide for $Tb^{3+}$. Also, since the greatest fold change in signal for pSAStide-terbium vs. SAStide-terbium was observed for the 1:1 complex, this represented the best ratio to maintain in subsequent kinase assays.

Measurements of the terbium luminescence lifetime were performed to characterize the photophysical properties of pSAStide-terbium and SAStide-terbium complexation. The hydration number (i.e. the number of water ligands (q) in the terbium coordination sphere) can be determined via the luminescence lifetime of the complex in $H_2O$ vs. $D_2O$, since the terbium excited state is quenched by the —OH vibrational overtones of $H_2O$ but not $D_2O$. Luminescence spectra for the pSAStide:$Tb^{3+}$ and SAStide:$Tb^{3+}$ complexes were collected in various ratios of $H_2O/D_2O$. The luminescence lifetimes were fitted to a single exponential decay and were determined to be 2.02 ms and 2.48 ms in $H_2O$ and $D_2O$ respectively for pSAStide:$Tb^{3+}$. These lifetimes lead to a q value of 0.12 for the phosphopeptide complex, indicating nearly an absence of $H_2O$ in the inner coordination sphere of terbium at equilibrium. The unphosphorylated SAStide:$Tb^{3+}$ had a comparably shorter lifetime in $H_2O$ at 1.88 ms and a longer lifetime $D_2O$ of 2.92 ms resulting in a q value of 0.66. These data suggest the SAStide:$Tb^{3+}$ contain closer to one $H_2O$ in the coordination sphere at equilibrium, resulting in more quenching of the terbium excited state, which manifested as a shorter lifetime. These differences are likely related to the greater luminescence intensity observed for the phosphorylated vs. unphosphorylated peptide, and also to the longer lifetime of the phosphopeptide that enabled gating of the signal for better dynamic range for discriminating the phosphorylated from unphosphorylated species using time-resolved signal collection.

The quantum yield for the pSAStide-terbium complex was determined using diffusion-enhanced energy transfer from the complex to fluorescein isothiocyanate (FITC). Luminescence emission spectra were collected in the presence of varying concentrations of FITC with increasing delay times. The time-resolved emission spectra and corresponding lifetime plots display an increase in emission intensity and a simultaneous decrease in the lifetime with increasing concentrations of FITC, and the quantum yield calculated from these data was 0.34.

Quantitative Detection of Syk Kinase Activity Using $Tb^{3+}$ Sensitization. To demonstrate the use of SAStide:$Tb^{3+}$ as a biosensor for quantitative detection of Syk activity, a calibration curve was established using mixed ratios of SAStide and pSAStide in the presence of the kinase assay components and quenching buffer conditions ($MgCl_2$, BSA, ATP, $NaVO_4$, protease inhibitors, piceatannol, DMSO, urea) at concentrations sufficient to mimic an appropriate background matrix for a kinase assay measurement (FIG. 3A). Luminescence emission spectra were collected for the various SAStide/pSAStide ratios and the area under the curves were integrated. Controls showed limited interference from the components of the kinase assay and quenching conditions. The calibration curve demonstrated that the emission spectral area increased linearly and was well correlated with increasing percent phosphorylation (FIG. 3B). However, there was an increase in the basal signal in the absence of pSAStide (relative to mixtures of just peptide and simple buffers) that was likely due to complexation of terbium with ATP. The three phosphate groups of ATP can provide an appropriate coordination environment and adenosine provides the appropriate chromophore for excitation ($\lambda_{ex}$=259 nm), giving rise to some background even with time-resolved measurements. Compared to detection of pSAStide vs. SAStide in HEPES buffer alone, this increase in background signal reduced the signal to noise ratio (S/N) by half (FIG. 1C compared to FIG. 3B). However, despite this decrease excellent S/N (15.3:1) was still achieved.

The limit of detection (LOD) for phosphorylation was 3.8±0.51%, defined as the percentage of pSAStide that gave a signal area corresponding to 3x the standard deviation greater than the baseline for unphosphorylated SAStide in the quenched kinase reaction buffer (the negative control). The limit of quantification (LOQ) for phosphorylation was 7.4±0.52%, defined as the percentage of pSAStide that gave a signal area 10x the standard deviation greater than the signal in the negative control. The Z′ factor and the signal window (SW) were also calculated to determine if this sensor would be appropriate for use in a high throughput screening (HTS) assay. The Z' factor should be between 0.5 and 1 for an assay to be considered appropriated for HTS, as assays with a Z' factor in this range exhibit a large dynamic ranges and wide separation of positive and negative results. Assays with a SW greater than 2 are also considered appropriate for HTS assays. Both parameters were calculated from the mean emission and standard deviation of the spectral area from triplicate measurements of the negative control SAStide in the in vitro assay buffer and the positive control pSAStide in the same conditions. The Z' factor and SW were determined to be 0.82 and 14.63, respectively, indicating that time-resolved terbium luminescence detection of SAStide phosphorylation is an appropriate method for HTS assays.

Detection of Syk activity in vitro was accomplished using Syk-EGFP immunoprecipitated from engineered DT40 chicken B-cells with the kinase reaction buffer and quenching conditions described above. After pre-incubation of the enzyme with the kinase reaction mixture, SAStide substrate was added and aliquots of the reaction were quenched at various time points in urea (to denature the enzyme). $Tb^{3+}$ was added and time-resolved luminescence was measured (FIG. 3C). The areas under the emission spectra were calculated, the percent phosphorylation was interpolated from the calibration curve and plotted against time (FIG. 3D). These data show that enzymatic phosphorylation of SAStide can be detected using time-resolved $Tb^{3+}$ luminescence. As a control to verify phosphorylation, an additional aliquot was used for detection of phosphorylation using an ELISA-based chemifluorescent assay (Supporting Information Figure S9).

Figures 4, 4A, 4B:
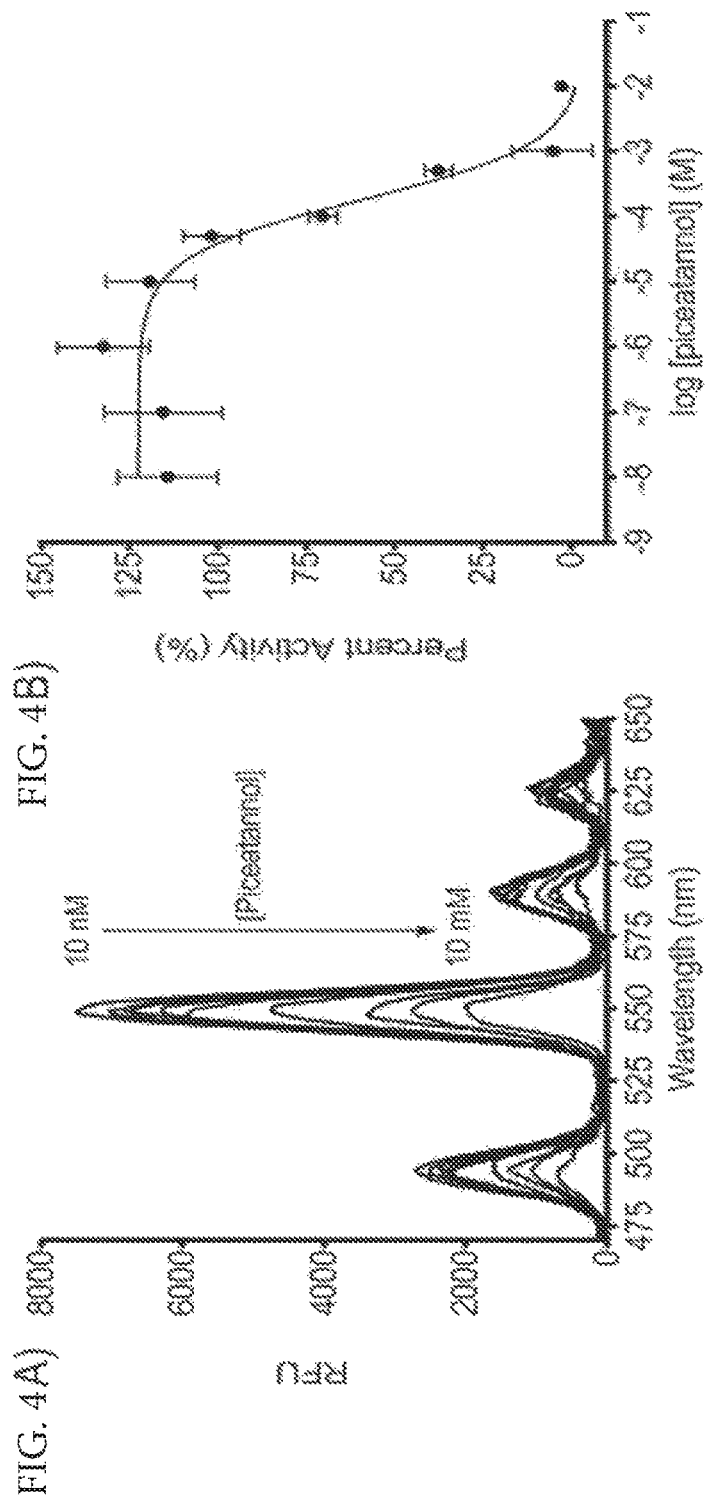
FIG. 4A shows in vitro Syk kinase assay luminescence emission spectra.
FIG. 4B is a plot showing dose-response inhibition of Syk by piceatannol.

The potential of this strategy for use in inhibitor screening was also evaluated. The effect of the Syk inhibitor piceatannol was assayed in a dilution series from 10 nM to 10 mM. Luminescence emission spectra were collected and integrated (FIG. 4A). The areas were normalized to the DMSO control and reported as percent activity. The observed $IC_{50}$ for piceatannol was 178±1.4 µM (FIG. 4B), consistent with that found in the literature. The Z' factor and SW were determined in the context of the dose-response inhibition assay, calculated from the standard deviation and mean from the normalized percent activity from triplicate measurements of the negative control (10 mM piceatannol) and the positive controls (10 nM-500 µM piceatannol). Over all the positive controls the Z' factor was greater than 0.5 and the SW was greater than 2, demonstrating that the application of pSAStide:$Tb^{3+}$ is appropriate as a HTS tool in practice.

Time-resolved $Tb^{3+}$ luminescence measurements were demonstrated to substantially increase signal to noise and thus dynamic range for quantitative analysis of peptide phosphorylation. Time-resolved luminescence detection has been employed in FRET-based assays for kinase activity (e.g. the LanthaScreen® assay from Life Technologies), however these assays rely on $Tb^{3+}$ chelation by a macrocyclic carrier conjugated to an anti-phosphosite antibody coupled with a fluorescently labeled substrate, and $Tb^{3+}$ itself is not involved in binding to the phosphorylated product of the kinase reaction. Therefore the LanthaScreen® technique depends on antibody availability and is an indirect, "off-line" measure of substrate phosphorylation. Exploiting the binding and sensitization of $Tb^{3+}$ directly with a phosphorylated substrate is essentially "label-free," since neither antibodies nor fluorophore labels are required. Time-resolved measurements significantly improved the signal to noise of detection compared to steady-state measurements by minimizing background signal. The ability to discriminate between the coordination environments for $Tb^{3+}$ binding to the unphosphorylated vs. phosphorylated peptides based on luminescence lifetime facilitated the improvement we observed in distinguishing between species. Accordingly, phosphorylation of the Syk substrate peptide SAStide could be applied for rapid, quantitative and sensitive detection of Syk kinase activity and inhibition by small molecule inhibitors with little to no interference from the components of the kinase reaction.

Besides the specific application to Syk kinase described here, this strategy has broad significance for detecting phosphorylation using lanthanide sensitization. Time-resolved detection should expand the possibilities for other peptide- and protein-based lanthanide sensitization approaches to achieve better dynamic range and sensitivity. This allows for leveraging existing $Tb^{3+}$-sensitizing substrates for other kinases, as well as open a new avenue for development of novel substrates to achieve high-throughput compatibility for other kinase targets important in therapeutic development, that otherwise may not have provided sufficient signal to noise with steady-state measurements.

Identification of Kinase Specific Peptide Substrates Using Informatics

Figure 5:
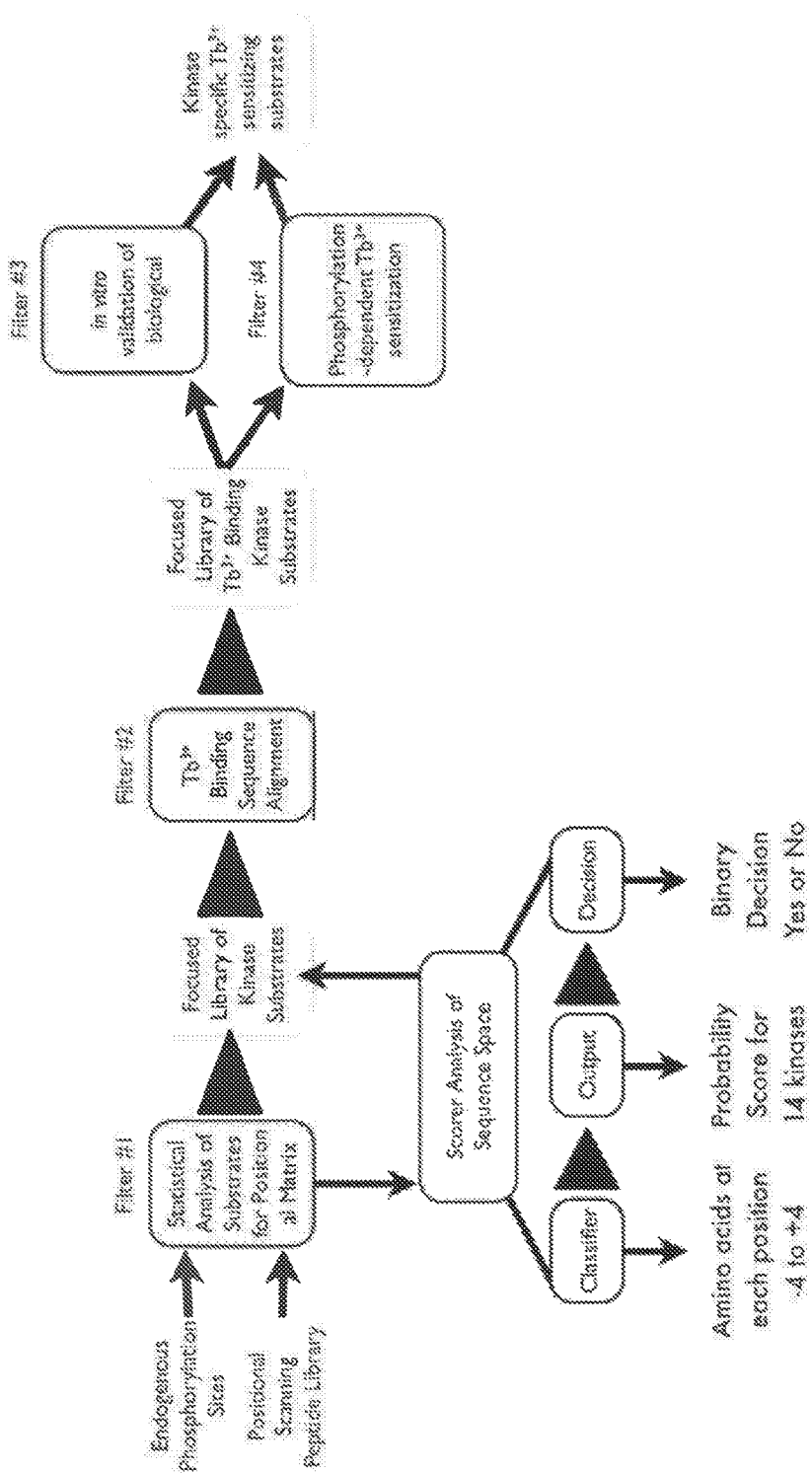
FIG. 5 is a schematic representation of a bioinformatics strategy for identifying tyrosine kinase peptide substrates.

For each kinase studied, a positional matrix was calculated as described above and a biosensor was designed to contain an optimized substrate or recognition sequence. These sequences were identified and optimized through a bioinformatic approach, represented schematically in FIG. 5. This method uses a positional probabilities matrix of amino acids about the phosphorylation sites of known biological substrates as well as empirical effects of amino acids from positional scanning peptide libraries to generate of positional scoring matrix (PMS). This matrix was used to guide the generation of a focused library of possible kinase specific peptide substrates. The focused library was then filtered based PSM scores classifying the sequences as substrate or nonsubstrates as well as specific or nonspecific substrates; all nonspecific or nonsubstrate sequences were removed from the library. The remaining sequences were filtered again based on sequence alignment with known terbium sensitizing peptides resulted in a more compressed library of potential kinase specific peptide substrates that also could potentially sensitize terbium luminescence (Table 1). The N and C-terminal portions of the substrates were modified by the addition of acidic residues to fulfill the requirements for terbium binding.

TABLE 1

| Kinase | Sequence | Abl | Arg | Btk | Csk | Fyn | Hck | Jak2 |
| --- | --- | --- | --- | --- | --- | --- | --- | --- |
| Btk | ELDAYLENE (SEQ ID NO: 14) | 0.0612 | 0 | 95.6392 | 0.006 | 0.2253 | 0.0012 | 0.0008 |
| | ELAGYLENE (SEQ ID NO: 15) | 0.0346 | 0.0638 | 93.7059 | 1.7044 | 0.062 | 0 | 0.0008 |

TABLE 1-continued

| Kinase | Sequence | | | | | | | |
|---|---|---|---|---|---|---|---|---|
| | ELDVYEEQL (SEQ ID NO: 16) | 1.2227 | 0.0761 | 49.6728 | 1.153 | 0.4552 | 0.2007 | 0 |
| | ELDVYEQT (SEQ ID NO: 17) | 0.4478 | 0.0031 | 77.3199 | 7.8338 | 0.0542 | 1.4037 | 0.0008 |
| Src Family | DEDIYEELD (SEQ ID NO: 18) | 20.6833 | 35.8182 | 19.6472 | 65.0808 | 97.1283 | 0.386 | 0 |
| | EGDVYDFVE (SEQ ID NO: 19) | 35.6824 | 4.8361 | 26.3009 | 1.4652 | 9.9397 | 98.3974 | 0.3513 |
| | NINDVYEQPE (SEQ ID NO: 20) | 85.2393 | 36.6505 | 0.3917 | 11.6312 | 31.2519 | 0.3714 | 0.0083 |
| | EEDVYDMPD (SEQ ID NO: 21) | 9.2966 | 88.9174 | 0.5655 | 0.4834 | 94.2591 | 39.9093 | 15.2417 |
| | EADVYDMPD (SEQ ID NO: 22) | 5.8425 | 82.204 | 0.0148 | 0.0395 | 80.3145 | 33.3778 | 23.201 |
| | DLDIYEELD (SEQ ID NO: 23) | 1.4851 | 0.7 | 39.4363 | 7.7841 | 87.8142 | 0 | 0 |
| | EAHVYDMMD (SEQ ID NO: 24) | 0.7811 | 9.6421 | 0 | 0.0016 | 6.185 | 0.2233 | 2.8372 |
| Jak2 | DPDRYIRTE (SEQ ID NO: 25) | 8.2503 | 0.1254 | 0.0031 | 0 | 0.0033 | 0.428 | 90.603 |
| | EGDRYLKLE (SEQ ID NO: 26) | 0.49 | 0.0627 | 1.3431 | 0 | 2.3798 | 0.8529 | 98.9811 |
| | EDGRYVQLD (SEQ ID NO: 27) | 6.4805 | 92.1246 | 0.0039 | 0.2689 | 11.2798 | 0.0025 | 99.3638 |
| | PKPRYVQLD (SEQ ID NO: 28) | 1.3358 | 42.9285 | 0.0335 | 0.039 | 6.3076 | 0 | 93.3284 |
| Abl | DEVAYQAPF (SEQ ID NO: 29) | 92.7371 | 38.9107 | 0.0031 | 9.4929 | 27.2398 | 26.9169 | 0.0025 |
| | DFIRYHFWV (SEQ ID NO: 30) | 5.0133 | 99.7691 | 0 | 0 | 0 | 0.0012 | 0 |
| | DHIFYIPV (SEQ ID NO: 31) | 96.8949 | 0.9753 | 0.1122 | 0.0125 | 2.7383 | 0.0325 | 0.06 |
| | DHIFYHIPV (SEQ ID NO: 32) | 92.9239 | 32.2272 | 0.0047 | 0 | 3.4669 | 0.046 | 0.0217 |
| Syk | DEEDYEEPD (SEQ ID NO: 1) | 58.0722 | 81.7725 | 0.8413 | 51.0911 | 17.5158 | 0.0184 | 0.0008 |

| Kinase | Sequence | Lck | Lyn | Pyk2 | Src | Syk | Yes |
|---|---|---|---|---|---|---|---|
| Btk | ELDAYLENE (SEQ ID NO: 14) | 0.0057 | 0.061 | 0.1556 | 1.8777 | 3.5421 | 0 |
| | ELAGYLENE (SEQ ID NO: 15) | 0.0872 | 0.0066 | 0.0006 | 0.2035 | 0.509 | 0 |
| | ELDVYEEQL (SEQ ID NO: 16) | 0.4667 | 0.0825 | 22.3633 | 21.3577 | 3.841 | 4.2402 |
| | ELDVYVEQT (SEQ ID NO: 17) | 0.9273 | 0.0244 | 54.4835 | 6.0868 | 2.8502 | 0.126 |
| Src Family | DEDIYEELD (SEQ ID NO: 18) | 99.273 | 99.982 | 86.9454 | 99.205 | 95.6083 | 99.8831 |
| | EGDVYDFVE (SEQ ID NO: 19) | 74.5148 | 96.3223 | 99.2952 | 88.5987 | 1.3542 | 94.7683 |
| | NINDVYEQPE (SEQ ID NO: 20) | 88.3116 | 12.3235 | 8.0806 | 93.3962 | 2.0012 | 75.5539 |
| | EEDVYDMPD (SEQ ID NO: 21) | 97.8776 | 74.7765 | 99.9145 | 98.5624 | 92.6192 | 79.0648 |
| | EADVYDMPD (SEQ ID NO: 22) | 82.6225 | 18.1129 | 93.562 | 95.027 | 66.061 | 31.6134 |
| | DLDIYEELD (SEQ ID NO: 23) | 90.435 | 87.8526 | 57.5102 | 90.4999 | 86.1128 | 33.0636 |
| | EAHVYDMMD (SEQ ID NO: 24) | 3.6951 | 3.9692 | 15.6708 | 93.0073 | 9.7643 | 0.1196 |
| Jak2 | DPDRYIRTE (SEQ ID NO: 25) | 0 | 0.09 | 0 | 0.4496 | 0.18281 | 0.0192 |
| | EGDRYLKLE (SEQ ID NO: 26) | 0.0255 | 0.9411 | 0.0096 | 0.5649 | 9.6434 | 0.1037 |
| | EDGRYVQLD (SEQ ID NO: 27) | 0.8727 | 0.1078 | 2.5882 | 16.505 | 0.497 | 0.3881 |
| | PKPRYVQLD (SEQ ID NO: 28) | 0.1415 | 0.0282 | 0.511 | 0.399 | 0.0032 | 0.008 |
| Abl | DEVAYQAPF (SEQ ID NO: 29) | 0.0017 | 1.2011 | 5.5276 | 17.1958 | 21.3202 | 38.6511 |
| | DFIRYHFWV (SEQ ID NO: 30) | 0 | 0.0047 | 0 | 0.0172 | 0 | 0 |
| | DHIFYIPV (SEQ ID NO: 31) | 0 | 0.2108 | 0 | 0.0119 | 0.3369 | 0.0016 |
| | DHIFYHIPV (SEQ ID NO: 32) | 0 | 0.0103 | 0 | 0.004 | 0.0026 | 0.0016 |
| Syk | DEEDYEEPD (SEQ ID NO: 1) | 41.0265 | 99.0182 | 13.0189 | 96.9995 | 99.983 | 97.5226 |

Detection of kinase activity using the novel sequences identified in the method disclosed herein is accomplished by three physical changes in the biosensors following phosphorylation. Phosphorylation of the biosensor results in the shift of the excitation wavelength from 275 nm for tyrosine to 266 nm for phosphotyrosine, binding affinity increases from micromolar to nanomolar, and the hydration number of the phosphopeptide-terbium complex is reduced due to the completion of the coordination sphere. All of these physical changes result in the increased luminescence intensity and lifetime of the phosphorylated form of the biosensor compared to the unphosphorylated biosensor.

Design and Validation of a Src Family Kinase Peptide Biosensor

The development of a Src family kinase peptide biosensor was performed by analysis of substrates for the individual members of the Src-family including Src, Lyn, Hck, Fyn and Yes tyrosine kinases. Unlike the other kinases the redundancy in substrate preference amongst these family members made it difficult to discern selectivity for each. The motif identified for these kinases was [D/E]-[D/E]-[D/E]-[I/L/V]-Y-[G/A/V/D/E]-[D/E/I/S/T]-[F/I/L/V]-[X].

The use of two different sequences GGEEDEDI-YEELDEPGGK$_{biotin}$GG (SEQ ID NO:45) and GGDNEGD-VYDFVEDGGK$_{biotin}$ (SEQ ID NO:46), designated Src family artificial substrate peptide A and B (SFAStide-A and SFAStide-B) respectively, was further explored.

Scores Versus the Substrate Efficiency

Scoring using the combined PM/PSPL algorithm was performed on six sequences that ranked in the top quartile of all possible permutations of the Src family motif. These peptides were synthesized and tested in in vitro kinase assays (conditions as before) using ELISA-based readout for detection. For Src kinase, it was observed that the scoring represented the empirical results if a threshold for determining a "positive" was set between a score of 99 and 96. In other words, both of the peptides that scored >99 for Src were efficient substrates, while those scoring <99 were not. Lyn predictions were not quite as accurate (with a >99 scoring sequence not being phosphorylated). The difference may be due to the number of input "positives" in the training dataset, which is larger for Src (at 167 known substrates) but relatively small for Lyn (at 48 known substrates). This underscores the importance of empirical validation to developing an efficient substrate when large datasets are not available. Even when large datasets are available, empirical testing can help to define the score cutoff that should be used as a threshold. Results of the evaluation of Src-family substrates are shown in FIG. 6. The sequences of potential substrates (DEDIYEELD (SEQ ID NO:18), DEDVYEELD (SEQ ID NO:38), DEDDYVDVD (SEQ ID NO:39), DEEDYGDVD (SEQ ID NO:40), DEDDYEDVD (SEQ ID NO:41), DEDDYEDID (SEQ ID NO:42), and DKDIYEELD (SEQ ID NO:43) and scores for Lyn vs. Src are shown in FIG. 6A.

FIG. 6B shows an ELISA readout for a time course from Lyn kinase assays using three of the peptides, and Src kinase assays for seven peptides are shown in FIG. 6C.

Characterization of Src Kinase Family-based Specificity

Figure 7:
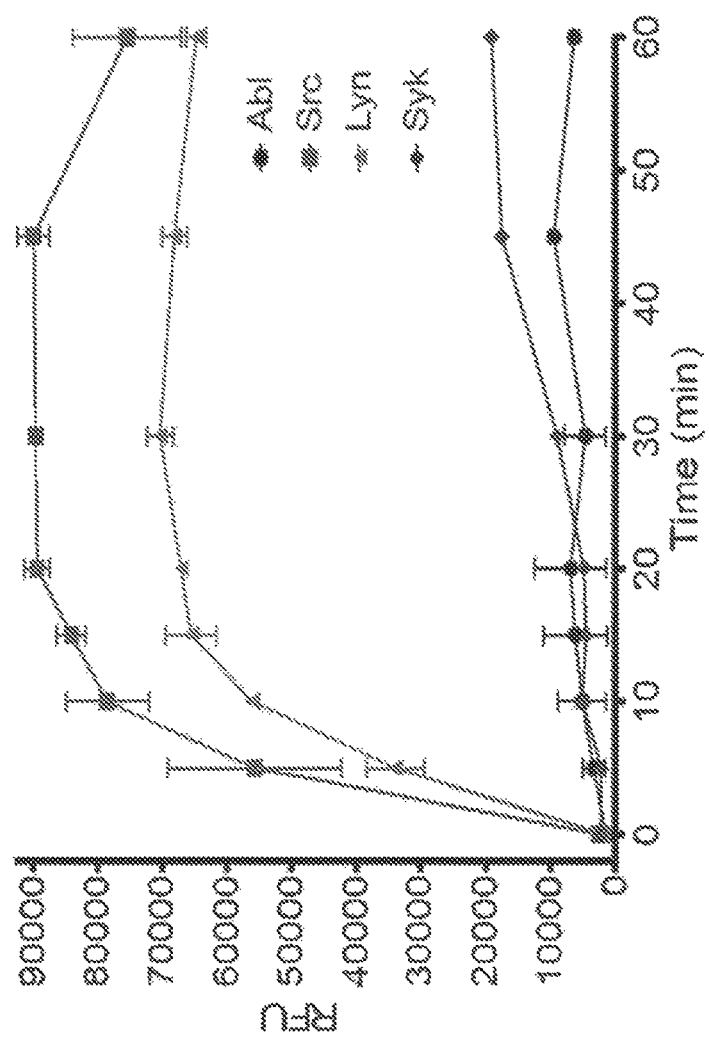
FIG. 7 is an ELISA readout for timecourse assays Src, Lyn, Abl, and Syk using SFAStide.

To evaluate the specificity of SFAStide-A in vitro kinase assays were performed with a small panel of kinases including Abl, Src, Hck and Syk. Phosphorylation of the biosensor was detected using an ELISA-based chemifluorescent assay. FIG. 7 shows that The Src-family tyrosine kinases Lyn and Src will phosphorylate SFAStide-A efficiently, whereas the non-Src-family tyrosine kinases c-Abl and Syk will not.

To evaluate the terbium luminescence increase of the biosensors both phosphorylated and unphosphorylated forms were synthesized and steady-state luminescence of each 1:1 Tb$^{3+}$ complex was measured with excitation at 266 nm through a monochromator. Excitation at 266 nm is the orthogonal wavelength for the phosphorylated forms and exhibited strong Tb$^{3+}$ sensitization and the unphosphorylated forms displayed weaker luminescence. While unphosphorylated signal was somewhat mitigated by using 266 nm excitation energy, there was still weak but significant luminescence from unphosphorylated form of the biosensor so the signal to noise (comparing the phosphorylated and unphosphorylated biosensor luminescence) was low (2:1) for both biosensors. However, time-resolved measurements significantly improved the signal to noise to 11:1 and 14:1 for SFAStideA and SFAStideB respectively, demonstrating that again, taking advantage of the increase in Tb$^{3+}$ luminescence lifetime in the presence of phosphotyrosine vs. unphosphorylated tyrosine improved the ability to detect phosphorylated forms. The improvement in the signal to noise ratio was accomplished by allowing the short-lived signal of the unphosphorylated peptide to decay prior to collection.

Binding affinities were determined using Tb$^{3+}$ luminescence as a measure of complexation. Terbium was titrated in the presence of 1 μM pSFAStide(A/B) or SFAStide(A/B) and luminescence emission spectra were collected and integrated. The binding curves displayed a hyperbolic increase in luminescence with increasing terbium concentrations from 0-50 μM (representing a ratio of 1:1 peptide/terbium), with saturation between 1-50 μM characteristic of one site binding. The calculated K$_d$ for pSFAStideA:terbium complex represented by the hyperbolic curve was 0.77 μM, which is comparable to the affinities reported for other terbium binding peptides. The unphosphorylated SFAStideA:terbium complexation displayed significantly weaker binding; exhibited a K$_d$ of 3.93 μM (5-fold weaker than for the phosphorylated peptide). These results demonstrate that phosphorylation increased the affinity of SFAStideA for Tb$^{3+}$. Likewise, pSFAStideB displayed a K$_d$ of 1.79 μM and SFAStideB demonstrated a K$_d$ of 2.50 μM (1.4-fold weaker than the phosphorylated form). Also, since the greatest fold change in signal for pSFAStideA-terbium vs. SFAStideA-terbium was observed, this substrate was selected for subsequent kinase assays.

To evaluate the potential of pSFAStideA for use as a biosensor for quantitative detection of Src-family kinase activity, a calibration curve was established using mixed ratios of SFAStideA and pSFAStideA in the presence of the kinase assay components and quenching buffer conditions (MgCl$_2$, BSA, ATP, DMSO, urea) at concentrations sufficient to mimic an appropriate background matrix for a kinase assay measurement. Luminescence emission spectra were collected for the various SFAStideA/pSFAStideA ratios and the area under the curves were integrated. The calibration curve demonstrated that the emission spectral area increased linearly and was well correlated with increasing percent phosphorylation.

The limit of detection (LOD) for phosphorylation was 7.9%, defined as the percentage of pSFAStideA that gave a signal area corresponding to 3× the standard deviation greater than the baseline for unphosphorylated SFAStideA in the quenched kinase reaction buffer (the negative control). The limit of quantification (LOQ) for phosphorylation was 21.8%, defined as the percentage of pSFAStideA that gave a signal area 10× the standard deviation greater than the signal in the negative control. The Z' factor and the signal window (SW) were also calculated to determine if this sensor would be appropriate for use in a high throughput screening (HTS) assay. The Z' factor should be between 0.5 and 1 for an assay to be considered appropriated for HTS, as assays with a Z' factor in this range exhibit a large dynamic ranges and wide separation of positive and negative results. Assays with a SW greater than 2 are also considered appropriate for HTS assays. Both parameters were calculated from the mean emission and standard deviation of the spectral area from triplicate measurements of the negative control SFAStideA in the in vitro assay buffer and the positive control pSFAStideA in the same conditions. The Z' factor and SW were determined to be 0.79 and 13.7, respectively, indicating that time-resolved terbium luminescent detection of SFAStideA phosphorylation is an appropriate method for HTS assays.

Activity of Hck (a Src-family kinase) in vitro was assayed using recombinant Hck with the kinase reaction buffer and quenching conditions described above. After pre-incubation of the enzyme with the kinase reaction mixture, the SFAStideA substrate was added and aliquots of the reaction were quenched at various time points in urea (to denature the enzyme). $Tb^{3+}$ was added and time-resolved luminescence was measured. The areas under the emission spectra were calculated, the percent phosphorylation was interpolated from the calibration curve and plotted against time. These data show that enzymatic phosphorylation of SFAStideA can be detected using time-resolved $Tb^{3+}$ luminescence.

Evaluation of SFAStideA for use in inhibitor screening.

The effect of the Src family kinase inhibitor nilotinib was assayed in a dilution series from 10 pM to 100 µM. Luminescence emission spectra were collected and integrated. The areas were normalized to the DMSO control and reported as percent activity. The observed $IC_{50}$ for nilotinib was 195 nM, consistent with that found in the literature. The Z' factor and SW were determined in the context of the dose-response inhibition assay, calculated from the standard deviation and mean from the normalized percent activity from triplicate measurements of the negative control (100 µM nilotinb) and the positive controls (10 pM-1 µM nilotinib). Over all the positive controls the Z' factor was greater than 0.5 and the SW was greater than 2 demonstrating that the application of pSFAStideA:$Tb^{3+}$ maintains its appropriateness as a HTS tool in practice.

Design and validation of an Abl peptide sensor

Bioinformatic analysis of substrate sequence preference revealed Abl displayed a substrate motif of [E/D]-[E/D/H/P/V]-[I/V]-[I/F/V]-Y-[A/Q/D]-[P/T]-[F/P/V]-[D/P]. This motif is in agreement with previous reports of kinase substrate motifs; however, some novel features were extracted from the input data that were unique to the analysis including the identification of glutamine at the +1 position as a preferable residue in the recognition sequence. Comparing the preferred residues at the +1 position with the other kinases in the method only Csk displays the same preference at this position. To demonstrate the ability of this method to identify novel kinase specific substrates for Abl capable of sensitizing terbium the sequence GGDEDDNDEVAY-QAPFEDGGK$_{biotin}$GG (SEQ ID NO:36), Abl artificial substrate peptide (ABStide), was synthesized.

Figure 8:
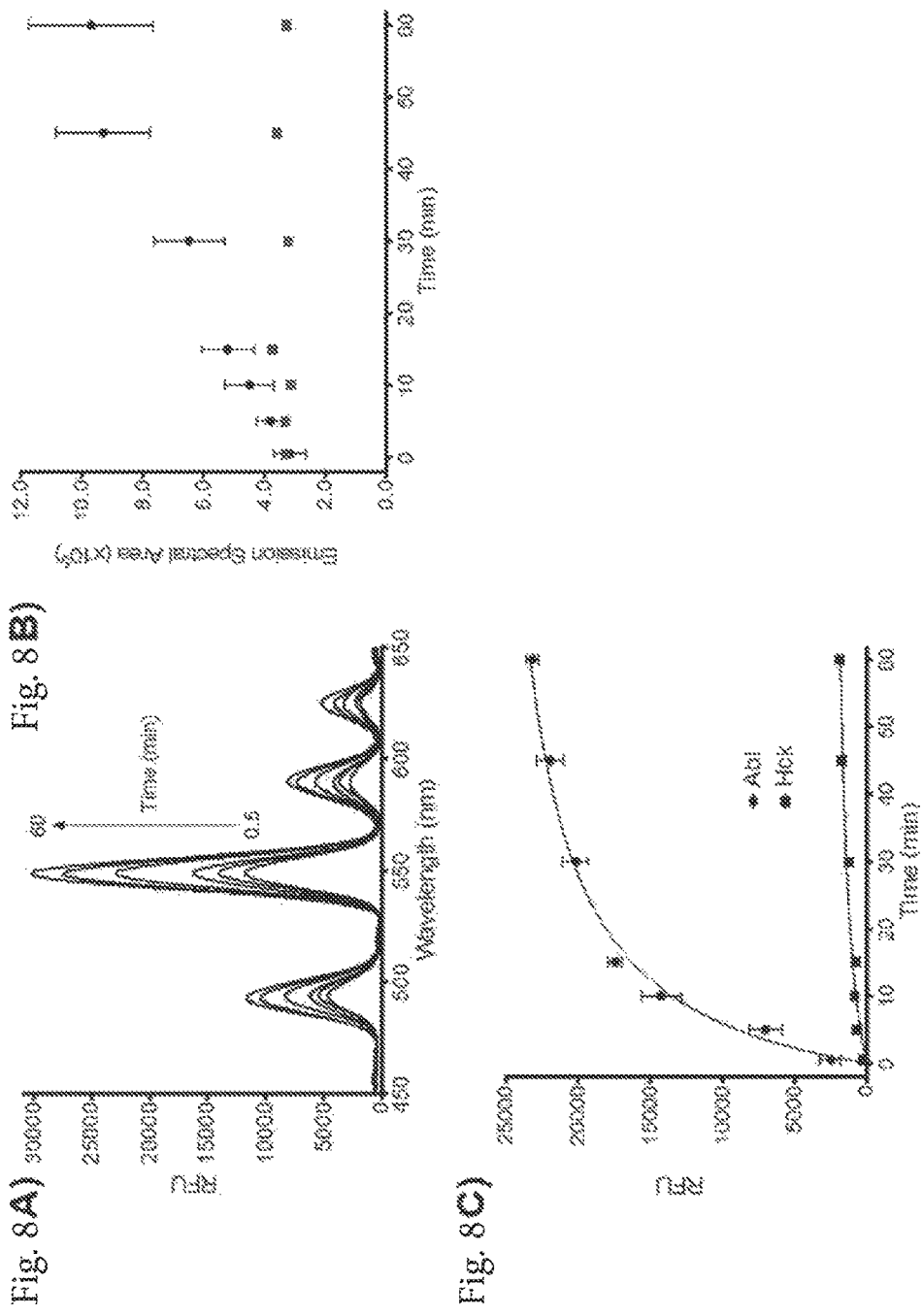
FIG. 8A is a luminescence emission spectra from an in vitro Abl kinase assay using ABStide.
FIG. 8B is a plot of in vitro Abl kinase assay luminescence emission spectra area.
FIG. 8C is an ELISA readout for a timecourse assay of Abl kinase using ABStide.

ABStide specificity was evaluated using in vitro kinase assay demonstrated that ABStide was specific for Abl against the Src-family kinase, Hck. These results were shown by terbium-sensitized luminescence (FIG. 8A and FIG. 8B) and confirmed by ELISA-based Amplex Red chemifluorescent assay (FIG. 8C).

Characterization of Bcl-Abl biosensor uptake and phosphorylation.

Uptake and phosphorylation of the Bcr-Abl biosensor peptide in a patient-derived CML model cell line K562 was evaluated using Western blot. To confirm that intracellular Abl signaling was not disrupted, cell lysates were probed to examine the phosphorylation status of the Bcr-Abl autophosphorylation site and the endogenous Abl substrates STAT5 and CrkL. Cells were cultured to log phase growth then treated with the Abl biosensor EAIYAAPFAKKK$_{(\gamma\text{-}biotin)}$G-βNpa-GCGGAPTYSPPPPPG-GRKKRRQRRRLL (SEQ ID NO:37) in the presence or absence of either imatinib or the phosphatase inhibitor pervanadate for 5, 30 or 60 minutes. The cells were then harvested and lysed in detergent buffer containing EDTA, phosphatase inhibitors, and protease inhibitors before being flash frozen in liquid nitrogen. Lysates were processed as described above, separated by SDS-PAGE and analyzed by Western blot using a two-color LiCOR scanner for quantitative detection of IR-dye labeled secondary antibodies and streptavidin (to measure total peptide signal via the biotinylated residue). The peptide was readily taken up into K562 cells and phosphorylated. As expected, phosphorylation was inhibited in the presence of imatinib and stabilized in the presence of pervanadate. In the presence of pervanadate, observed peptide levels decreased over time. Because the lysis buffer contained a cocktail of protease inhibitors, it was unlikely that this degradation was occurring post-lysis. Consistent with previous reports, the decrease in peptide over time was found to be due to degradation of the peptide once it enters the intracellular environment.

Figure 3:
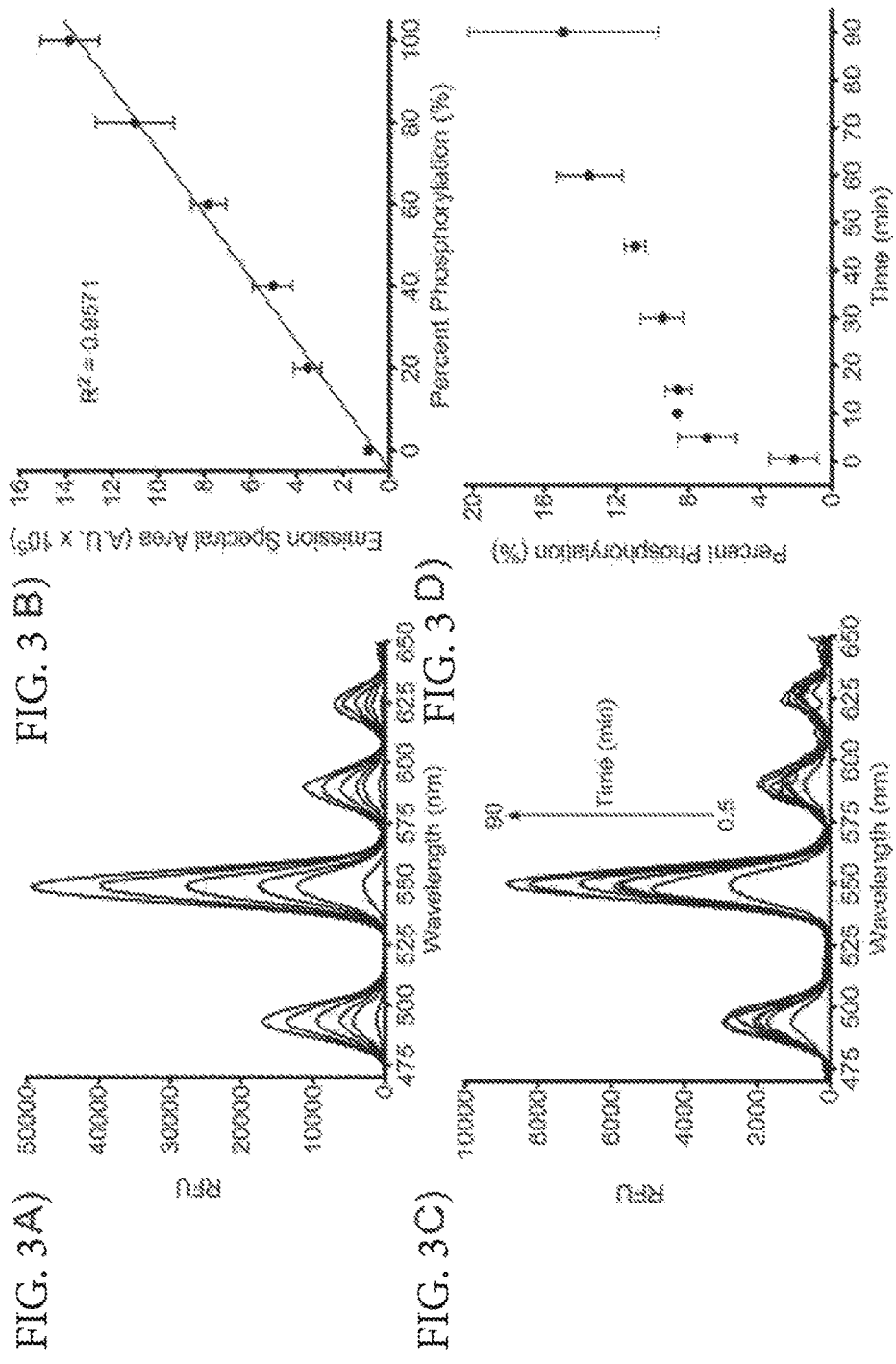
FIG. 3A shows pSAStide-$Tb^{3+}$ luminescence emission spectra in the presence of the quenched Syk in vitro kinase assay buffer.
FIG. 3B shows emission spectral area calibration curve based on percent phosphorylation in vitro.
FIG. 3C shows in vitro Syk kinase assay luminescence emission spectra.
FIG. 3D shows interpolated percent phosphorylation from Syk in vitro kinase assay.

This was tested by exploiting the biotin affinity tag to capture peptide from lysate generated after 5 min incubation and analyzed it by MALDI-TOF/TOF mass spectrometry. Within just 5 min of exposure to cells (as well as approximately 2-3 min additional processing time for cell harvesting), essentially no intact peptide was observed, even for samples treated with peptide alone (FIG. 3). Several fragments were detected (along with photo-induced ion chemistry intermediates arising from the UV laser ionization inherent in MALDI-TOF analysis, also observed with the intact peptide as further discussed in the supporting information) and identified by MS/MS analysis to arise from C-terminal degradation. In particular, the cell permeability tag, TAT, was almost completely removed from the C-terminus. However, the N-terminal "reporter" sequence (which contains the phosphorylation site for Bcr-Abl) was still intact—that is, no corresponding N-terminally truncated fragments were observed. Peptide in lysates was enriched using streptavidin-coated magnetic nanoparticles through the peptide's biotinylated reporter segment. From this workflow, phosphorylated and unphosphorylated peptides could be detected by MALDI-TOF in linear positive and negative mode, however reproducibility and signal to noise were poor (example spectra provided in the supporting information)—a problem not previously encountered when working with engineered cell lines. Accordingly, a more sensitive detection strategy was needed to robustly quantify the degree of biosensor peptide phosphorylation by Bcr-Abl. In future work, it may be possible to improve sensitivity and reduce ambiguity by eliminating the photocleavable linker and stabilizing the peptide biosensor via the incorporation of residues resistant to proteolysis.

Development of the MRM method for quantitative analysis. MRM was evaluated to for improved sensitivity in the context of trypsin-digested whole cell lysate from cells incubated with the biosensor peptide. One advantage of this approach is that because the tryptic fragment arising from the "reporter" module of the biosensor is unnatural, it is not subject to confounding background from the native proteins in the cell lysate. Two transitions for each peptide were included in the development of the MRM method, to increase confidence in peptide identity. A calibration curve was established for quantitation of the MRM signal from the tryptic fragments of the biosensor peptide and its synthetically phosphorylated derivative, which were added 1:1 at various concentrations into trypsin-digested K562 lysate (1 µg/µl). Signals for both the modified and unmodified form of the Abl biosensor peptide were robust and linear between 5 and 250 fmol. Analytical coefficients of variation (CV) were between 1-26% (depending on the transition). One transition from each peptide was chosen for quantitative analysis based on its signal to noise and CV across the calibration range. Based on the ratios of these transitions, the ratio of signals for the phosphorylated and unphosphorylated peptides was approximately 1:1, with a CV of 4.3% across the entire concentration range, giving confidence in the analytical reproducibility for quantifying the percent phosphopeptide in a sample.

Analysis of Abl biosensor phosphorylation. To analyze biosensor phosphorylation, K562 cells were incubated with the biosensor for 5 minutes either alone or in the presence of Bcr-Abl inhibitor (imatinib) or phosphatase inhibitor (pervanadate) as described above. 1 µg of each cell lysate was analyzed using the MRM method described above. MRM signal data were extracted as chromatograms and the substrate peptide and its phosphorylated derivative were identified by the presence of both transitions in their respective peaks at the retention time expected for these analytes from the calibration curve analyses. Some background peaks were observed in each extracted chromatogram, however none of these exhibited signal for both transitions and the expected retention time. Because the intensities of the total ion chromatograms (TICs) for each analysis were not completely uniform, a characteristic, invariable peak in the TIC was integrated and used to calculate a correction factor for each MRM chromatogram. After this correction was applied, the peaks specific to the unphosphorylated and phosphorylated peptides were integrated and interpolated to determine the amount of unphosphorylated and phosphorylated peptides in each sample. As expected, both unphosphorylated and phosphorylated peptides were detected in the samples treated with peptide alone. No phosphorylated peptide was detected in the samples pre-treated with imatinib, and higher levels (relative to peptide alone) of phosphorylated peptide were detected in the samples treated with phosphatase inhibitor. Differences between % phosphorylation observed in the peptide only and peptide+pervanadate samples were statistically significant ($p<0.05$, one-way ANOVA with Tukey post-test), as well as being significantly different compared to the absence of phosphopeptide seen in the peptide+imatinib samples ($p=0.044$ and $0.025$, respectively, one sample t-test).

All peptides were detected at levels above both their LOD and LOQ. The fmol-scale levels of peptide detected here may represent the entirety of material taken up into cells and isolated by lysis, or it may represent the remaining reporter segment present after some degree of degradation. MALDI-TOF analysis of degradation indicated that N-terminal degradation did not appear to be taking place, however it is still possible that the fragments were just not observable. Nonetheless, MRM-based detection of the N-terminal tryptic fragment was for the most part reproducible: CVs for analyte quantification were acceptable (20% for unphosphorylated and 23% for phosphorylated species) for the samples treated with peptide alone. CVs for the imatinib and pervanadate treated samples were somewhat higher (~42% for total peptide detection, unphosphorylated plus phosphorylated, from each) and considerably higher (71%) for the amount of phosphopeptide detected in the pervanadate treated samples. Comparing these results to the Western blot detection, the CVs for streptavidin band intensities were lower for the peptide only and imatinib treated samples (11% each) but comparable (32%) for the pervanadate treated sample. CVs for the 4G10 signals of the peptide only (12%) and pervanadate (68%) samples were more similar to the CVs from MRM. For imatinib treated samples, 4G10 Western blot CVs were much higher due to the background intensity which was not a factor in the MRM analysis. While these two experiments and methods cannot necessarily be directly compared (for example, the analytical variabilities may be different between the two techniques, and the ratio of 4G10/streptavidin signal is uncalibrated and thus cannot give a % phosphopeptide), this at least shows that the results from MRM analysis are correlated with those observed using the traditional Western blot analysis. Based on the excellent analytical CVs obtained from the MRM calibration curve experiments, the higher CVs observed for the imatinib and pervanadate treated samples most likely reflect biological or sample processing and handling variability (e.g. peptide uptake, the enzymatic reaction taking place, level of phosphatase inhibition, and small differences in e.g. lysis and/or handling) rather than analytical variability. When self-normalized to represent the % phosphopeptide compared to total, CVs were within an acceptable range (20-40%) for all samples, given the biological variability involved in a cell-based enzyme activity assay.

Taken together, these results demonstrate that accurate and reproducible detection of Bcr-Abl biosensor peptide phosphorylation and inhibition in an intracellular assay. Using K562 cells as a human CML model system, substantial improvements in the lower detection limits for the assay read-out are shown compared to previous detection strategies. The amount of total sample analyzed (1 µg) is equivalent to approximately 15,000 cells, indicating that it is possible to achieve several orders of magnitude improvement in sensitivity compared to Western blot or MALDI-TOF detection. This level of sensitivity and technical reproducibility for the detection method should enable miniaturization of the assay procedure and application to clinical material.

It is claimed:

1. A biosensor comprising:
   a peptide substrate that includes a sequence selected from the group consisting of ELDAYLENE (SEQ ID NO:14), ELAGYLENE (SEQ ID NO:15), ELDVYEEQL (SEQ ID NO:16), ELDVYVEQT (SEQ ID NO:17), DEDIYEELD (SEQ ID NO:18), EGDVYDFVE (SEQ ID NO:19), NNDVYEQPE (SEQ ID NO:20), EEDVYDMPD (SEQ ID NO:21), EADVYDMPD (SEQ ID NO:22), DLDIYEELD (SEQ ID NO:23), EAHVYDMMD (SEQ ID NO:24), DPDRYIRTE (SEQ ID NO:25), EGDRYLKLE (SEQ ID NO:26), EDGRYVQLD (SEQ ID NO:27), PKPRYVQLD (SEQ ID NO:28), DEDVYEELD (SEQ ID NO:38), DEDDYEDID (SEQ ID NO:42), DKDIYEELD (SEQ ID NO:43), DEDDYGDVD (SEQ ID NO:44), GGEEDEDIYEELDEPGGK$_{biotin}$GG (SEQ ID NO:45), and GGDNEGDVYDFVEDGGK$_{biotin}$GG (SEQ ID NO:46), the substrate specific for a tyrosine kinase selected from the group consisting of Btk, Src family kinases, and Jak2; and at least one of a cell penetrating peptide and an affinity tag, the cell penetrating peptide and/or tag linked directly or indirectly to the peptide substrate.

2. The biosensor of claim 1, wherein the peptide substrate includes a sequence selected from the group consisting of ELDAYLENE (SEQ ID NO:14), ELAGYLENE (SEQ ID NO:15), ELDVYEEQL (SEQ ID NO:16), and ELDVYVEQT (SEQ ID NO:17).

3. The biosensor of claim 1, wherein the peptide substrate includes a sequence selected from the group consisting of DEDIYEELD (SEQ ID NO:18), EGDVYDFVE (SEQ ID NO:19), NNDVYEQPE (SEQ ID NO:20), EEDVYDMPD (SEQ ID NO:21), EADVYDMPD (SEQ ID NO:22), DLDIYEELD (SEQ ID NO:23), and EAHVYDMMD (SEQ ID NO:24).

4. The biosensor of claim 1, wherein the peptide substrate includes a sequence selected from the group consisting of DPDRYIRTE (SEQ ID NO:25), EGDRYLKLE (SEQ ID NO:26), EDGRYVQLD (SEQ ID NO:27), and PKPRYVQLD (SEQ ID NO:28).

5. The biosensor of claim 1, wherein the biosensor comprises the sequence GGEEDEDIYEELDEPGGK$_{biotin}$GG (SEQ ID NO:45).

6. The biosensor of claim 1, wherein the biosensor comprises the sequence GGDNEGDVYDFVEDGGK$_{biotin}$GG (SEQ ID NO:46).

7. The biosensor of claim 1, wherein the cell penetrating peptide includes a sequence selected from the group consisting of GRKKRRQRRRPPQ (SEQ ID NO:47), RKKRRQRRR (SEQ ID NO:35), RQIKIWFQNRRMKWKK (SEQ ID NO:48), GWTLNSAGYLLGKINLKALAALAKKIL (SEQ ID NO:49), GALFLGFLGAAGSTMGAWSQPKKKRKV (SEQ ID NO:50), GALFLGFLGAAGSTMGA (SEQ ID NO:51), and EQNPIYWARYADWLFTTPLLLLDLALLVDADEGT (SEQ ID NO:52).

8. The biosensor of claim 1, wherein the affinity tag includes a moiety selected from the group consisting of biotin and His6 chemical groups.

* * * * *

SEQUENCE LISTING

<160> NUMBER OF SEQ ID NOS: 53

<210> SEQ ID NO 1
<211> LENGTH: 9
<212> TYPE: PRT
<213> ORGANISM: Artificial Sequence

```
<220> FEATURE:
<223> OTHER INFORMATION: Synthetic

<400> SEQUENCE: 1

Asp Glu Glu Asp Tyr Glu Glu Pro Asp
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Asp Glu Glu Asp Tyr Glu Glu Pro Asp Glu Pro
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Glu Glu Asp Asp Tyr Glu Ser Pro Asn
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Glu Glu Asp Ser Tyr Glu Ser Pro Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Glu Glu Asp Ser Tyr Asp Ser Pro Asn
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Glu Glu Asp Asp Tyr Glu Ser Pro Asn Glu Pro
1               5                   10

<210> SEQ ID NO 7
<211> LENGTH: 11
<212> TYPE: PRT
<213> ORGANISM: Artificial Sequence
<220> FEATURE:
```

<223> OTHER INFORMATION: Synthetic

<400> SEQUENCE: 7

Glu Glu Asp Ser Tyr Glu Ser Pro Asn Glu Pro
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Glu Glu Asp Ser Tyr Asp Ser Pro Asn Glu Pro
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Gly Gly Glu Glu Asp Asp Tyr Glu Ser Pro Asn Glu Pro Gly Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Gly Gly Glu Glu Asp Ser Tyr Glu Ser Pro Asn Glu Pro Gly Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Gly Gly Glu Glu Asp Ser Tyr Asp Ser Pro Asn Glu Pro Gly Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Gly Gly Asp Glu Glu Asp Tyr Glu Glu Pro Asp Glu Pro Gly Gly
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: Synthetic

```
<400> SEQUENCE: 13

Gly Gly Glu Glu Asp Ser Tyr Asp Ser Pro Asn Gly Gly
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Glu Leu Asp Ala Tyr Leu Glu Asn Glu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Glu Leu Ala Gly Tyr Leu Glu Asn Glu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Glu Leu Asp Val Tyr Glu Glu Gln Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Glu Leu Asp Val Tyr Val Glu Gln Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Asp Glu Asp Ile Tyr Glu Glu Leu Asp
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 19

Glu Gly Asp Val Tyr Asp Phe Val Glu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Asn Asn Asp Val Tyr Glu Gln Pro Glu
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Glu Glu Asp Val Tyr Asp Met Pro Asp
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Glu Ala Asp Val Tyr Asp Met Pro Asp
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Asp Leu Asp Ile Tyr Glu Glu Leu Asp
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Glu Ala His Val Tyr Asp Met Met Asp
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25
```

```
Asp Pro Asp Arg Tyr Ile Arg Thr Glu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Glu Gly Asp Arg Tyr Leu Lys Leu Glu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Glu Asp Gly Arg Tyr Val Gln Leu Asp
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Pro Lys Pro Arg Tyr Val Gln Leu Asp
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Asp Glu Val Ala Tyr Gln Ala Pro Phe
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Asp Phe Ile Arg Tyr His Phe Trp Val
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31
```

```
Asp His Ile Phe Tyr Ile Ile Pro Val
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Asp His Ile Phe Tyr His Ile Pro Val
1               5

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Asp Pro Asp Asn Glu Ala Tyr Glu Met Pro Ser Glu Glu Gly
1               5                   10

<210> SEQ ID NO 34
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (16)..(16)
<223> OTHER INFORMATION: Biotinylated Lysine
<220> FEATURE:
<221> NAME/KEY: MUTAGEN
<222> LOCATION: (19)..(19)
<223> OTHER INFORMATION: beta(nitrophenyl)alanine

<400> SEQUENCE: 34

Gly Gly Asp Glu Glu Asp Tyr Glu Glu Pro Asp Glu Pro Gly Gly Lys
1               5                   10                  15

Gly Gly Ala Arg Lys Lys Arg Arg Gln Arg Arg Arg
            20                  25

<210> SEQ ID NO 35
<211> LENGTH: 9
<212> TYPE: PRT
<213> ORGANISM: Human immunodeficiency virus type 1

<400> SEQUENCE: 35

Arg Lys Lys Arg Arg Gln Arg Arg Arg
1               5

<210> SEQ ID NO 36
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (21)..(21)
<223> OTHER INFORMATION: Biotinylated Lysine

<400> SEQUENCE: 36

Gly Gly Asp Glu Asp Asp Asn Asp Glu Val Ala Tyr Gln Ala Pro Phe
```

Glu Asp Gly Gly Lys Gly Gly
            20

<210> SEQ ID NO 37
<211> LENGTH: 41
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (12)..(12)
<223> OTHER INFORMATION: gamma-Biotinylated Lysine
<220> FEATURE:
<221> NAME/KEY: MUTAGEN
<222> LOCATION: (14)..(14)
<223> OTHER INFORMATION: beta(nitrophenyl)alanine

<400> SEQUENCE: 37

Glu Ala Ile Tyr Ala Ala Pro Phe Ala Lys Lys Lys Gly Ala Gly Cys
1               5                   10                  15

Gly Gly Ala Pro Thr Tyr Ser Pro Pro Pro Pro Gly Arg Lys
            20                  25                  30

Lys Arg Arg Gln Arg Arg Arg Leu Leu
        35                  40

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Asp Glu Asp Val Tyr Glu Glu Leu Asp
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Asp Glu Asp Asp Tyr Val Asp Val Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Asp Glu Glu Asp Tyr Gly Asp Val Asp
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

```
<400> SEQUENCE: 41

Asp Glu Asp Asp Tyr Glu Asp Val Asp
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Asp Glu Asp Asp Tyr Glu Asp Ile Asp
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic

<400> SEQUENCE: 43

Asp Lys Asp Ile Tyr Glu Glu Leu Asp
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Asp Glu Asp Asp Tyr Gly Asp Val Asp
1               5

<210> SEQ ID NO 45
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (18)..(18)
<223> OTHER INFORMATION: Biotinylated Lysine

<400> SEQUENCE: 45

Gly Gly Glu Glu Asp Glu Asp Ile Tyr Glu Glu Leu Asp Glu Pro Gly
1               5                   10                  15

Gly Lys Gly Gly
            20

<210> SEQ ID NO 46
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (17)..(17)
<223> OTHER INFORMATION: Biotinylated Lysine

<400> SEQUENCE: 46

Gly Gly Asp Asn Glu Gly Asp Val Tyr Asp Phe Val Glu Asp Gly Gly
```

```
<210> SEQ ID NO 47
<211> LENGTH: 13
<212> TYPE: PRT
<213> ORGANISM: Human immunodeficiency virus type 1

<400> SEQUENCE: 47

Gly Arg Lys Lys Arg Arg Gln Arg Arg Arg Pro Pro Gln
1               5                   10

<210> SEQ ID NO 48
<211> LENGTH: 16
<212> TYPE: PRT
<213> ORGANISM: Drosophila melanogaster

<400> SEQUENCE: 48

Arg Gln Ile Lys Ile Trp Phe Gln Asn Arg Arg Met Lys Trp Lys Lys
1               5                   10                  15

<210> SEQ ID NO 49
<211> LENGTH: 27
<212> TYPE: PRT
<213> ORGANISM: Artificial Sequence
<220> FEATURE:
<223> OTHER INFORMATION: Synthetic

<400> SEQUENCE: 49

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 50
<211> LENGTH: 27
<212> TYPE: PRT
<213> ORGANISM: Human immunodeficiency virus type 1

<400> SEQUENCE: 50

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Gly Ala Leu Phe Leu Gly Phe Leu Gly Ala Ala Gly Ser Thr Met Gly
1               5                   10                  15

Ala

<210> SEQ ID NO 52
<211> LENGTH: 34
<212> TYPE: PRT
<213> ORGANISM: Artificial Sequence
<220> FEATURE:
<223> OTHER INFORMATION: Synthetic
```

```
<400> SEQUENCE: 52

Glu Gln Asn Pro Ile Tyr Trp Ala Arg Tyr Ala Asp Trp Leu Phe Thr
1               5                  10                  15

Thr Pro Leu Leu Leu Leu Asp Leu Ala Leu Leu Val Asp Ala Asp Glu
                20                  25                  30

Gly Thr

<210> SEQ ID NO 53
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (17)..(17)
<223> OTHER INFORMATION: Biotinylated Lysine

<400> SEQUENCE: 53

Gly Gly Asp Glu Glu Asp Tyr Glu Glu Pro Asp Glu Pro Gly Gly Lys
1               5                  10                  15

Gly Gly
```